(12) United States Patent
Kim et al.

(10) Patent No.: US 12,138,367 B2
(45) Date of Patent: Nov. 12, 2024

(54) PLASMA-ASSISTED FLEXIBLE MULTI-SCALE TOPOGRAPHIC PATCHES FOR ENGINEERING CELLULAR BEHAVIOR AND TISSUE REGENERATION

(71) Applicant: INDUSTRY FOUNDATION OF CHONNAM NATIONAL UNIVERSITY, Gwangju (KR)

(72) Inventors: Jangho Kim, Gwangju (KR); Woochan Kim, Gwangju (KR)

(73) Assignee: INDUSTRY FOUNDATION OF CHONNAM NATIONAL UNIVERSITY, Gwangju (KR)

(*) Notice: Subject to any disclaimer, the term of this patent is extended or adjusted under 35 U.S.C. 154(b) by 815 days.

(21) Appl. No.: 17/124,768

(22) Filed: Dec. 17, 2020

(65) Prior Publication Data

US 2022/0008621 A1    Jan. 13, 2022

(30) Foreign Application Priority Data

Jul. 9, 2020   (KR) .......................... 10-2020-0084809

(51) Int. Cl.
| | | |
|---|---|---|
| *A61L 27/50* | (2006.01) | |
| *A61L 27/16* | (2006.01) | |
| *B29C 59/02* | (2006.01) | |
| *B29C 71/04* | (2006.01) | |

(Continued)

(52) U.S. Cl.
CPC .............. *A61L 27/50* (2013.01); *A61L 27/16* (2013.01); *B29C 59/02* (2013.01); *B29C 71/04* (2013.01); *A61L 2400/12* (2013.01); *A61L 2400/18* (2013.01); *A61L 2430/02* (2013.01); *B29K 2101/12* (2013.01); *B29L 2031/753* (2013.01); *Y10T 428/2457* (2015.01)

(58) Field of Classification Search
CPC ...... A61L 27/50; A61L 27/16; A61L 2400/12; A61L 2400/18; A61L 2430/02; A61L 2/14; B05D 3/141; B05D 3/142; B05D 3/145; Y10T 428/2457
USPC .......................................................... 428/167
See application file for complete search history.

(56) References Cited

U.S. PATENT DOCUMENTS

| | | | | |
|---|---|---|---|---|
| 2016/0017268 A1* | 1/2016 | Kim | ........................ | C12M 41/46 435/287.1 |
| 2020/0055041 A1* | 2/2020 | Kim | ................... | G01N 33/4836 |

FOREIGN PATENT DOCUMENTS

| | | | | |
|---|---|---|---|---|
| KR | 20110094753 A | * | 8/2011 | |
| KR | 10-1186093 B1 | | 9/2012 | |
| KR | 10-1385509 B1 | | 5/2014 | |

(Continued)

OTHER PUBLICATIONS

Translation of KR20110094753A (bib, description and claims). (Year: 2011).*

(Continued)

*Primary Examiner* — Catherine A. Simone
(74) *Attorney, Agent, or Firm* — PLEECHAE IP, LLC

(57) ABSTRACT

The present invention provides a scaffold for tissue regeneration and a method of manufacturing the same. The scaffold for tissue regeneration of the present invention includes grooves and ridges formed on one surface thereof, wherein the grooves or ridges have a plurality of nanopores formed thereon, thereby providing an environment suitable for attachment, differentiation, growth, and migration of cells. Therefore, the scaffold may be effectively used as a material for tissue regeneration.

13 Claims, 20 Drawing Sheets

(51) Int. Cl.
  *B29K 101/12*   (2006.01)
  *B29L 31/00*   (2006.01)

(56) References Cited

FOREIGN PATENT DOCUMENTS

| KR | 10-2018-0006321 A | 1/2018 |
| KR | 10-2019-0060414 A | 6/2019 |

OTHER PUBLICATIONS

Min-Suk Kook, et al., "Effect of oxygen plasma etching on pore size-controlled 3D polycaprolactone scaffolds for enhancing the early new bone formation in rabbit calvaria", Dental Materials Journal, 2018; 37(4): 599-610.

Kontziampasis, Dimitrios, et al.,"Cell array fabrication by plasma nanotexturing.", Proceedings vol. 8765, Bio-MEMS and Medical Microdevices, 2013, Article No. 87650B.

Guillemette, Maxime D, et al.,"Surface topography induces 3D self-orientation of cells and extracellular matrix resulting in improved tissue function.", ntegrative Biology, 2009, vol. 1, pp. 196-204.

\* cited by examiner

PLASMA-ASSISTED FLEXIBLE MULTI-SCALE TOPOGRAPHIC PATCHES FOR ENGINEERING CELLULAR BEHAVIOR AND TISSUE REGENERATION

CROSS-REFERENCE TO RELATED APPLICATION AND CLAIM OF PRIORITY

This application claims priority to Korean Patent Applications No. 10-2020-0084809 filed on Jul. 9, 2020 in the Korean Intellectual Property Office (KIPO), the entire disclosure of which is incorporated by reference herein.

BACKGROUND

1. Field of the Invention

The present invention relates to a scaffold for tissue regeneration, and a method of manufacturing the same.

2. Description of the Related Art

Tissue regeneration abilities of a human body are very complex, and regeneration abilities are very limited because of a complex tissue structure thereof. The human body has the possibility of regeneration at the time of tissue damage due to various cells including stem cells and constitutive environments, but for reasons such as an accident, disease, aging, and the like, a case of exceeding the limits of regenerative function may occur. Due to an increase of various diseases and accidents together with growth of aging populations in recent years, a necessity for regeneration of organ tissues is increasing rapidly as the organ tissues of a living body are being pushed beyond the limits of the bodies regeneration abilities.

Tissue engineering is a field of regenerative medicine ranging from cells to artificial organs, and is recognized as an important technology in life sciences and medical fields in the future based on studies of biological and engineering technologies from biomaterials to inorganic materials, which may help the restoration of tissues or organs. Various methods are being studied in order to understand the correlation between the structure and function of the living body, and furthermore, achieve purposes of restoring, maintaining and improving the functions of the human body by making substitutes for living bodies and then implanting the same into the body. One of key technologies in tissue engineering is to create a support or scaffold which plays a role of supporting so that cells may grow well. Unlike a two-dimensional membrane or capsule, the scaffold has a three-dimensional shape, and refers to a space in which all cells in the body having a three-dimensional structure may be attached thereto, and then differentiated and proliferated.

The scaffold plays a very important role in bio-tissue engineering. In detail, the scaffold plays an important role in the growth of cells seeded in a porous structure and cells migrating from the surrounding tissues. Most cells in the human body are adherent cells that grow attached, and if there is no place to attach, the cells may not grow and die. Therefore, the scaffold should provide an environment suitable for attachment, differentiation, growth, and migration of cells.

Accordingly, the present inventors have confirmed that topographic features and nanopores of an extracellular matrix (ECM) promote cell behavior and tissue regeneration, and therefore, the present invention has been completed on the basis of the above confirmation.

SUMMARY

It is an object of the present invention to provide a scaffold for tissue regeneration.

In addition, another object of the present invention is to provide a method of manufacturing a scaffold for tissue regeneration.

To achieve the above objects, the following technical solutions are adopted in the present invention.

1. A scaffold for tissue regeneration including: a plurality of grooves and ridges on one surface thereof, wherein the grooves or ridges have a plurality of nanopores formed thereon.

2. The scaffold according to above 1, wherein the grooves and the ridges extend in one direction.

3. The scaffold according to above 1, wherein the grooves and the ridges have a width of 100 to 900 nm, respectively.

4. The scaffold according to above 1, wherein a ratio of widths of the grooves and the ridges is 1:0.5 to 1.5.

5. The scaffold according to above 1, wherein the ridge has a height of 100 to 900 nm from the groove.

6. The scaffold according to above 1, wherein the nanopore has a diameter of 50 to 200 nm.

7. The scaffold according to above 1, wherein the one surface has a carboxyl group (O=C=O), a carbonyl group (C=O), or a hydroxyl group (—OH).

8. The scaffold according to above 1, wherein the scaffold is made of one or more materials selected from the group consisting of polyurethane acrylate (PUA) resin, polyvinyl alcohol resin, polyethylene resin, polypropylene resin, polyethylene glycol resin, poly(L-lactide-co-glycolide) resin, polycaprolactone (PCL) resin, polylactic acid (PLA) resin, polyglycolic acid (PGA) resin, chitosan, gelatin, collagen, and a combination thereof.

9. The scaffold according to above 1, wherein the tissue is epithelial tissue, muscle tissue, tendon tissue, bone tissue or cartilage tissue.

10. A method of manufacturing a scaffold for tissue regeneration including: forming a plurality of grooves and ridges on one surface of a base film; and performing oxygen plasma treatment on the one surface of the base film to form a plurality of nanopores on the one surface.

11. The method according to above 10, wherein the base film is one or more materials selected from the group consisting of polyurethane acrylate (PUA) resin, polyvinyl alcohol resin, polyethylene resin, polypropylene resin, polyethylene glycol resin, poly(L-lactide-co-glycolide) resin, polycaprolactone (PCL) resin, polylactic acid (PLA) resin, polyglycolic acid (PGA) resin, chitosan, gelatin, collagen, and a combination thereof.

According to the present invention which relates to a scaffold for tissue regeneration and a method of manufacturing the same, the scaffold for tissue regeneration of the present invention includes grooves and ridges on one surface thereof, wherein the grooves or ridges have a plurality of nanopores formed thereon, thereby providing an environment suitable for attachment, differentiation, growth, and migration of cells. Therefore, the scaffold may be effectively used as a material for tissue regeneration.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
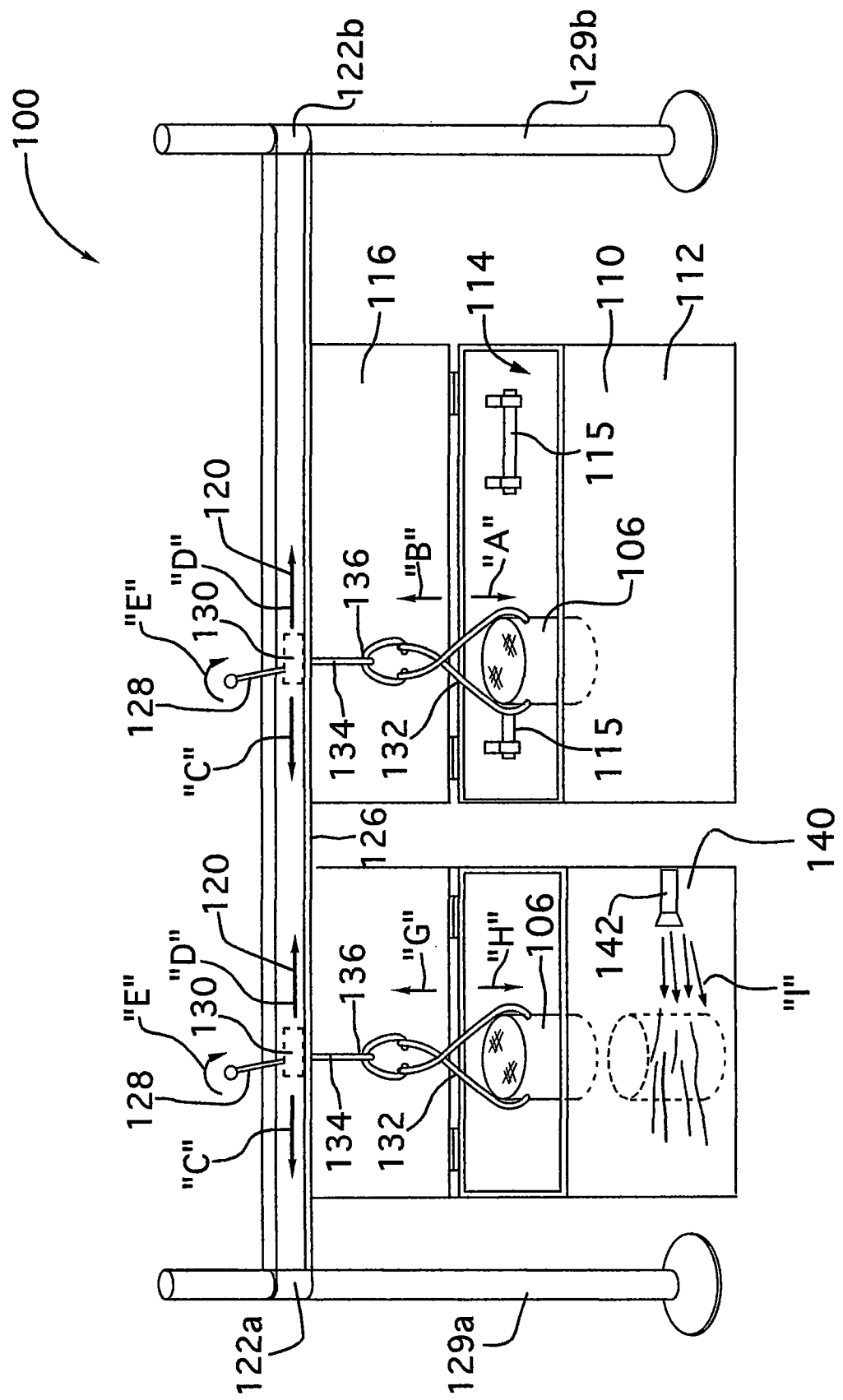
FIGS. 1-5 are schematics of the fabrication and characterization of a N-FN patch. (1) Fabrication of a polycaprolactone (PCL)-based FN patch. Inspired by the high aligned and well-organized nano-topography of the native ECM, the PCL-based FN patch was fabricated using capillary force lithography (CFL). Plasma surface modification on the surface of the FN patch. The surface of the patches was modified using $N_2$ plasma reaction gas. (2) SEM images of the surface of FN patches treated by $N_2$ plasma reaction gas under various times. (3) FT-IR analysis of the N-FF and N-FN patches treated plasma under various times. (4) XPS survey scans and (5) high-resolution N1s XPS spectra of FN patches and 30-min N-FN patches.

Hereinafter, the present invention will be described in detail.

The present invention relates to a scaffold for tissue regeneration which includes a plurality of grooves and ridges on one surface thereof, wherein the grooves or ridges have a plurality of nanopores formed thereon.

A structure of an extracellular matrix (ECM) in living tissues usually exhibits topographic characteristics (topographic density, and local density) having valleys arranged in one direction with various lengths on the nanometer scale, whereas the scaffold of the present invention may include grooves and ridges, thereby having a structure similar to the topographical characteristics of such an extracellular matrix (ECM).

The scaffold of the present invention may include a plurality of grooves and ridges. The number of grooves and ridges is not particularly limited, and may be appropriately selected depending on types of tissues to be regenerated and the number or density of cultured cells.

The grooves and ridges may extend in one direction. By including the plurality of grooves and ridges which extend in one direction, cells may be aligned/orientated in one direction. Accordingly, by regulating behaviors such as cell movement and cell extension, it is possible to adjust cellular tissues and promote regeneration thereof. The grooves and ridges extend in one direction, and specifically, may be arranged in parallel to each other. In the present disclosure, the term "parallel" means including not only an arrangement of completely parallel but also a level that can be regarded as substantially arranged in parallel.

Shapes of the groove and the ridge are not particularly limited so long as they allow cells to be arranged in a certain direction, and may be, for example, shapes whose longitudinal sections are each independently triangular, square, pentagonal, circular, or elliptical, but preferably, the shapes thereof are a square in terms of a more regular cell arrangement.

Widths of the grooves and the ridges may be appropriately selected so as to have a width similar to the arrangement of the extracellular matrix (ECM) of the tissue to be regenerated. For example, the grooves and the ridges may have a width of 100 nm to 900 nm or 600 nm to 850 nm, respectively. In this case, a ratio of the widths of the grooves and the ridges is, for example, 1:0.5 to 1.5, preferably 1:0.7 to 1.3, and more preferably 1:0.8 to 1.2 within the above range in terms of regular arrangement.

In addition, a height of the ridge from the groove may be appropriately selected so as to have a height similar to the arrangement of the extracellular matrix of the tissue to be regenerated. For example, the ridge may have a height of 100 to 900 nm or 600 nm to 850 nm.

The scaffold of the present invention may variously control topographical density by variously adjusting the widths and heights of the grooves and ridges. Accordingly, the scaffold has a density similar to the arrangement of the extracellular matrix of the tissue to be regenerated, such that the cells may be arranged in accordance with the target tissue, and cell characteristics such as a moving speed, cell elongation, stress fiber distribution, cytoskeleton, size of focal adhesion (FA), length of fibronectin fiber bundle or wound dressing rate may be controlled.

The scaffold of the present invention has a plurality of nanopores on the grooves or ridges.

The nanopore may form a nanostructure similar to the microenvironment of the extracellular matrix (ECM) of the tissue to be regenerated, thus to further improve cell affinity and hydrophilic properties, and thereby promoting attachment, proliferation and tissue regeneration of the cell.

The nanopores may be formed by performing oxygen plasma treatment. For example, when performing the oxygen plasma treatment on one surface of a base film including the grooves and ridges, the oxygen reacts with COOH— (carboxyl group) of PCL and the functional group on the surface is decomposed into $CO_2$ and $H_2O$, such that nanopores may be formed by etching and volatilization.

The nanopores may exist in various sizes. The number of nanopores is not particularly limited, and may be appropriately selected so as to have a structure similar to the structure of the extracellular matrix of the tissue to be regenerated by controlling an output, pressure or flow rate of oxygen plasma.

The nanopores may exist in various diameters. For example, the diameter thereof may be 50 to 200 nm, preferably 70 to 160 nm, and more preferably 90 to 120 nm. The diameter thereof may be appropriately selected so that cell attachment, cell proliferation, and tissue regeneration effects can be improved according to the tissue to be regenerated and its environment.

The nanopores may exist on the grooves and ridges of the surface of the material in a depressed form by the plasma treatment. In addition, it may be adjusted in a form having a penetrated hole depending on plasma output conditions (temperature, time and power) and the like.

Depending on the plasma treatment conditions of the pore, the shape and size thereof may be formed in various types and dimensions.

In addition, by adjusting a surface roughness of the material depending on the plasma treatment conditions, the scaffold may have properties capable of better adhering to the tissue to be regenerated, and an effect of improving the function of cells depending on the roughness may be achieved.

The scaffold of the present invention may have a carboxyl group (O=C—O), carbonyl group (C=O), or hydroxyl group (—OH) on one surface thereof. The functional group may be bonded to the grooves or ridges.

The scaffold of the present invention may be made of one or more materials selected from the group consisting of a polyurethane acrylate (PUA) resin, polyvinyl alcohol resin, polyethylene resin, polypropylene resin, polyethylene glycol resin, poly(L-lactide-co-glycolide) resin, polycaprolactone (PCL) resin, polylactic acid (PLA) resin, polyglycolic acid (PGA) resin, chitosan, gelatin, collagen, and a combination thereof. Herein, in terms of biocompatibility, the polyurethane acrylate (PUA) resin, polycaprolactone (PCL) resin, and poly(L-lactic-co-glycolide) resin are preferably used, and in terms of tissue regeneration, the polycaprolactone (PCL) resin is more preferably used, but it is not limited thereto.

The tissue to be regenerated is not particularly limited, but may be, for example, epithelial tissue, muscle tissue, tendon tissue, bone tissue or cartilage tissue.

In addition, the present invention relates to a method of manufacturing a scaffold for tissue regeneration including: forming a plurality of grooves and ridges on one surface of a base film; and performing $O_2$ plasma treatment on the one surface to form a plurality of nanopores on the one surface.

The base material may be one or more materials selected from the group consisting of polyurethane acrylate (PUA) resin, polyvinyl alcohol resin, polyethylene resin, polypropylene resin, polyethylene glycol resin, poly(L-lactide-co-glycolide) resin, polycaprolactone (PCL) resin, polylactic acid (PLA) resin, polyglycolic acid (PGA) resin, chitosan, gelatin, collagen, and a combination thereof, but is not limited thereto.

For example, the grooves and ridges may be formed in such a manner that: ridges having a height and width of a nano unit are formed on the base film at a predetermined interval, and then, valleys are formed between the ridges; valleys having a depth and width of a nano unit are formed on the base film at a predetermined interval, and then, ridges are formed between the valleys; or the base material is pressed by a mold having grooves and ridges, but it is not limited thereto.

Specifically, the grooves and ridges may be formed by capillary force lithography (CFL).

The capillary force lithography is a method of forming a pattern by pulling a polymer into an empty space of a mold using forces inherent to capillary action, such that grooves and ridge patterns may be formed in a fine and precise manner.

The mold may use, for example, a polyurethane acrylate (PUA) mold or a polydimethylsiloxane (PDMS) mold. The PUA (Young's modulus: 100 to 400 MPa) mold, and the PDMS (Young's modulus: 2 MPa) mold have different Young's modulus, such that the mold may be selected depending on the material used for manufacturing nanosized patterns using the capillary force lithography. If preparing nano patterns using the polyurethane acrylate (PUA) resin, polycaprolactone (PCL) resin or poly (L-lactide-co-glycolide) resin, more delicate patterns (patterns having a narrower interval) may be formed when using the PUA mold. Therefore, the scaffold for tissue regeneration of the present invention may be manufactured using the PUA mold.

The method of present invention includes performing oxygen plasma treatment on one surface of the base film to form a plurality of nanopores on the one surface.

The oxygen plasma treatment may be performed by appropriately selecting an output, pressure, or flow rate thereof so that nanopores having various forms of tissue to be regenerated are formed. Specifically, the oxygen plasma treatment may be performed with an output of 10 to 50 W, a pressure of 1 to 10 $e^{-1}$ Torr, or a flow rate of 10 to 50 sccm, but it is not limited thereto.

When performing the oxygen plasma treatment on one surface of the base film, a portion of the base film may be etched or volatilized to form nanopores. For nanopores, when performing oxygen plasma treatment on one surface of the base film including the grooves and ridges, oxygen may react with COOH— (carboxyl group) of PCL and the functional group is decomposed into $CO_2$ and $H_2O$ on the surface thereof, thereby forming nanopores by etching and volatilization.

Hereinafter, preferred embodiments will be described to more concretely understand the present invention.

1. Materials and Methods 1.1. Design and Fabrication of a Flexible Nano-Topographic (FN) Patch A droplet of ultraviolet (UV)-curable polyurethane acrylate (PUA) (Changsung Sheet, Korea) precursor solution with a photo-initiator was dropped onto a silicon master mold, on which nano-sized (800 nm) linear grooves and ridges were etched using conventional photolithography and reactive ion etching. The mold was then uniformly covered with a transparent poly (ethylene terephthalate) (PET; SKC, Korea) film utilizing capillary force. After the master mold was exposed to UV light ($\lambda$=352 nm, 40 w) for 60 s, the cured nanopatterned PUA replica was peeled off from the master mold using tweezers and again exposed to UV light overnight to eliminate any residual reactive acrylate groups. First, the nanopatterned PUA mother mold was attached to a Petri dish with the nanotopographic surface facing up. A polydimethyl siloxane (PDMS) pre-polymer (Sylgard 184 Silicon elastomer, Dow Corning, USA) was mixed with a 10% curing agent, poured onto the nanopatterned PUA mother mold in a Petri dish to a sufficient thickness (~1 cm), and baked at 70° C. for at least 6 h to ensure curing without any residue formation. The cured nanopatterned PDMS mold (800-nm ridges and grooves) was then peeled off from the PUA mother mold in the Petri dish. To fabricate the flexible flat (FF) patch as a control for comparison, a flat silicon wafer was attached to the Petri dish with the flat surface facing up. Similar to the fabrication protocol of the nanopatterned PDMS mold, the same PDMS pre-polymer was mixed with the 10% curing agent, poured onto the flat silicon wafer in the Petri dish to a sufficient thickness (~1 cm), and baked at 70° C. for at least 6 h to ensure curing without any residue formation. The cured flat-patterned PDMS mold was then peeled off from the flat silicon wafer in the Petri dish. Because of the surface charge of the silicon wafer, the nanotopographical PCL patch imprinted directly on the silicon wafer was not easily peel off. Therefore, we used the PDMS mold, whose surface is a negative charge, to easily peel off the PCL patches. In addition, heat and pressure applied in the fabrication process to fabricate the nanotopographical PCL patch can easily cause damage to the silicon wafer master mold. This limitation does not guarantee reproducibility to fabricate a large number of the nanotopographical PCL patches for various experiments. Therefore, to maintain reproducibility of the original nanostructure by minimizing damages, a mother molds were fabricated with PDMS and PUA, and then the nanotopographical PCL patches were indirectly fabricated using it.

PCL pellets (Mw: 80,000; Sigma-Aldrich, USA) were dissolved in dichloromethane using a magnetic stirrer, and a PCL solution of 18 wt % (wt/wt) in dichloromethane (Daejung Chemicals & Materials Co., Ltd, Korea) was prepared. A thin PCL patch was fabricated by spin-coating the PCL solution that was poured into a 1.5-mm circular glass on the vacuum cuck of the spin coater. The spin-coating condition was as follows: rotator speed of 3500 rpm, duration of 120 s, and acceleration time of 5 s. First, we fabricated the FF patch as a control group because the surface of the spin-coated PCL patch has irregular roughness that limits fabrication of an FN patch. The fabricated thin PCL patch was placed onto the silicon wafer substrate face-up to melt the PCL layer on a hot plate for 60 s at 80° C. The flat patterned PDMS mold was placed and embossed onto the pre-melted PCL layer by applying pressure with smooth finger force while heating at 80° C. for 2 min. After the thermal imprinting process, the assembly of the PCL layer on circular glass and PDMS molds was cooled at 25° C. for 30 min, and the PDMS mold was peeled off from the PCL layer on the circular glass, resulting in an FF patch. And then, FF patches were used to fabricate FN patches. The fabrication process of the FN patch is almost similar to that of FF patch, except that it uses a nanopattern PDMS mold. In this study, all patches were separated from the circular glass by washing with 70% ethanol for implantation in the in vivo study. The abbreviations for all samples in this work are as follows: flexible flat patch (FF patch), flexible nanotopographic patch (FN patch), $N_2$ gas plasma-treated flexible flat patch (N-FF patch), $N_2$ gas plasma-treated flexible nanotopographic patch (N-FN patch), $O_2$ gas plasma-treated flexible flat patch (O-FF patch), $O_2$ gas plasma-treated flexible multiscale nanotopographic patch (O-FMN patch)

1.2. Plasma Modification

The fabricated FF and FN patches were washed with ethanol and dried. Surface treatment of patches was carried out using a CUTE-1MP (Femto Science, Korea) low-pressure plasma system. Before processing, the empty chamber was cleaned for 5 min with $O_2$ gas plasma (30 W generation power, 60 sccm gas flow rate, and $5.52e^{-1}$ Torr pressure). $N_2$ and $O_2$ gas plasma treatments were performed for 1 min, 5 min, 10 min, 20 min, and 30 min each under 30 W generation power, 60 sccm gas flow rate, and $5.52e^{-1}$ Torr pressure.

1.3. Characteristics and Properties Analysis

N-FF and N-FN patches treated for 0, 1, 5, 10, 20, and 30 min were analyzed, and O-FF and O-FN patches treated for 0 and 30 min were analyzed using high-resolution field-emission scanning electron microscope (FE-SEM), Fourier transform-infrared spectroscopy (FT-IR), and X-ray photoelectron spectroscopy (XPS). FE-SEM images of the surface of all patches fabricated in this study were observed using a JSM-7500F microscope (Oxford, UK) at an acceleration voltage of 15.0 kV and average working distance of 8.8 mm. The samples were coated with platinum prior to morphological observation. Chemical characteristics of plasma-treated flat patches and plasma-treated nano-topographic patches were analyzed to confirm their chemical variation. The chemical bond structures were examined by FT-IR (Spectrum 400, USA). The surface chemical composition was analyzed using XPS (K-ALPHA+, Thermo Scientific, USA). The XPS survey spectra were recorded using a monochromatic Al Kα source (1486.67 eV) with a spot size of 200 μm and an electron take-off angle of 90°. The typical base pressure was below $2 \times 10^{-9}$ mbar. Survey spectra were recorded in the range of 0 to 1350.0 eV with a pass energy of 200 eV, step size of 1.0 eV, and dwell time of 10.0 ms.

1.4. Water Contact Angle Measurements

The static water contact angle of liquids was measured using customized camera systems with a Computer M1214-MP2⅔" Fixed Lens and analyzed using the ImageJ software. N-FF and N-FN patches treated for 0, 1, 5, 10, 20, and 30 min were analyzed, and O-FF and O-FN patches treated for 30 min were analyzed. For each measurement, 10 μl of water was drop-dispensed onto the surface over a time span of 1 min. The water contact angle was then measured as the tangent to the interface of the droplet on the patches. Measurements were repeated at least five times for each sample and averaged. All experiments were performed at room temperature.

1.5. Isolation and Culture of Tenocytes

The tendon tissue samples were collected from the supraspinatus tendon of patients during arthroscopic rotator cuff (RC) repair surgery after obtaining informed consent from patients at Chonnam National University Medical School and Chonnam National University Hospital. The tendon tissue samples were washed with phosphonate-buffered saline (PBS; Sigma-Aldrich, USA), cut into small pieces, and digested with mg/ml collagenase (Sigma-Aldrich, USA) in Dulbecco's modified Eagle's medium (DMEM; Cellgro, USA) at 37° C. for 16 h. After enzymatic digestion, equal volumes of DMEM were added to quench the collagenase and filtered through cell strainers (70-μm mesh). The filtered cell suspension was centrifuged at 1,500 rpm for 5 min. The cell pellets were resuspended and cultured in DMEM low-glucose (Cellgro, USA) supplemented with 10% fetal bovine serum (FBS; Cellgro, USA)) and 1% penicillin-streptomycin (GenDEPOT, Houston, TX, USA) at 37° C. in a 5% $CO_2$ atmosphere. The medium was changed every 3 days. All cells used in this work were at passage 4-6.

1.6. Cell Attachment and Proliferation Analysis

Tenocytes ($1 \times 10^4$ cells/samples) were seeded onto the samples and cultured for 6 h, 3 days (cell proliferation), and 5 days in DMEM containing 10% FBS and 1% antibiotics (Cellgro, USA) at 37° C. in a humidified atmosphere containing 5% $CO_2$. Quantitative analysis of cell proliferation on the samples was performed using a WST-1 assay (Premix WST-1 Cell Proliferation Assay System, Takara Bio Inc., Kusatsu, Japan). To confirm cell attachment, the patches were washed using PBS to remove any cells not attached to the scaffolds prior to quantitative analysis using the WST-1 assay.

1.7. Osteogenic Mineralization Analysis

Tenocytes ($4 \times 10^4$ cells/sample) were cultured for 14 days on samples in osteogenic differentiation medium (100 nM dexamethasone, 50 μm ascorbic acid, and 10 mm glycerol 2-phosphate in normal media). Alizarin Red S (Sigma-Aldrich, USA) staining was used to confirm the osteogenic differentiation (according to the degree of mineralization) of tenocytes on sample surfaces. The stained cells were de-stained with cetylpyridinium chloride (Sigma-Aldrich, USA), and the extracted stains were measured using an absorbance reader (iMark™ Microplate Absorbance Reader, Bio-Rad, Hercules, CA, USA) at 595 nm to quantify the osteogenic differentiation of tenocytes.

1.8. In Vivo Animal Study

In addition, the animal study was approved by the Ethics Committee of Chonnam National University. 6-week-old, male mouse (C57Bl/6N) were assigned into 4 groups of 4 each: Defect, Nano, N-FN patch and O-FMN. The mice were fully anesthetized with an intraperitoneal injection zoletil 0.006 cc/10 g and rumpun 0.004 cc/10 g, the heads were shaved and disinfected. The bones were exposed by incising the skin approximately 3.0 cm above the calvaria bone. The bone defects (diameter: 5 mm) were made on the one side of the revealed calvarial bone using an electric drill. Prepared patches (Diameter: 5 mm) were placed on the calvarial bone defect. After suturing the skin with sutures, the ambient temperature was raised, and mice were waked up from anesthesia. The mice were sacrificed 3 and 6 weeks after sur-gery to obtain tissues including the defect region and the calvarial bone.

1.9. Histological Observations and Evaluation

The proximal humerus including the greater tuberosity head with attached supraspinatus tendon of both shoulder of each rat was harvested. Specimens were fixed in neutral buffered 10% formalin (pH 7.4) and decalcified with Calci-Clear Rapid (National Diagnostics, Atlanta) for 2 weeks, and paraffin blocks were made in the repair site including supraspinatus tendon and greater tuberosity. Sections (4 μm thickness) were cut in the coronal plane and stained with hematoxylin and eosin (H&E) and Masson's trichrome. We assessed cellularity, collagen fiber continuity, orientation, density, and maturation of the tendon to bone interface, and we also evaluated the inflammation rate around patch at the tendon-to-patch interface. Images were captured and acquired using an Aperio ImageScope (Leica, Ca, USA) software.

The calvarial bone tomography was performed using Skyscan001172 (Skyscan, Konitch, Belgium) micro computed tomography (Micro-CT) at a resolution of 11.38 pixels and exposure time of 316 ms, with an energy source of 80 kV and current of 124 uA. An average of 488 slices of calvarial bone was scanned. The Micro-CT images were analyzed using MIMICS 14.0 3D imaging software (Materialise's Interactive Medical Image Control System, Leuven, Belgium). The calvarial bone specimens were fixed in 10% formalin and decalcified in a 0.5 M EDTA (pH 7.4) solution at room temperature for 7 days. After the specimens were embedded in paraffin, cut into 5 μm-thick sections. And then, they stained with hematoxylin and eosin (H&E). Images were obtained by the Aperio Images Scope (Leica, Ca, USA) software.

1.10. Statistical Analysis

All quantitative data are presented as the mean standard deviation. Unpaired Student t-tests were used for the statistical analysis of the cell adhesion, viability, and differentiation results. To compare three or more conditions, a one-way ANOVA was performed. P-value of less than 0.05 was considered to be statistically significant. Statistical analyses of the Micro-CT were performed using Kruskal-Wallis testing with SPSS software.

2. Results 2.1. Design and Fabrication of FN and N2-FN Patches

Figure 2:
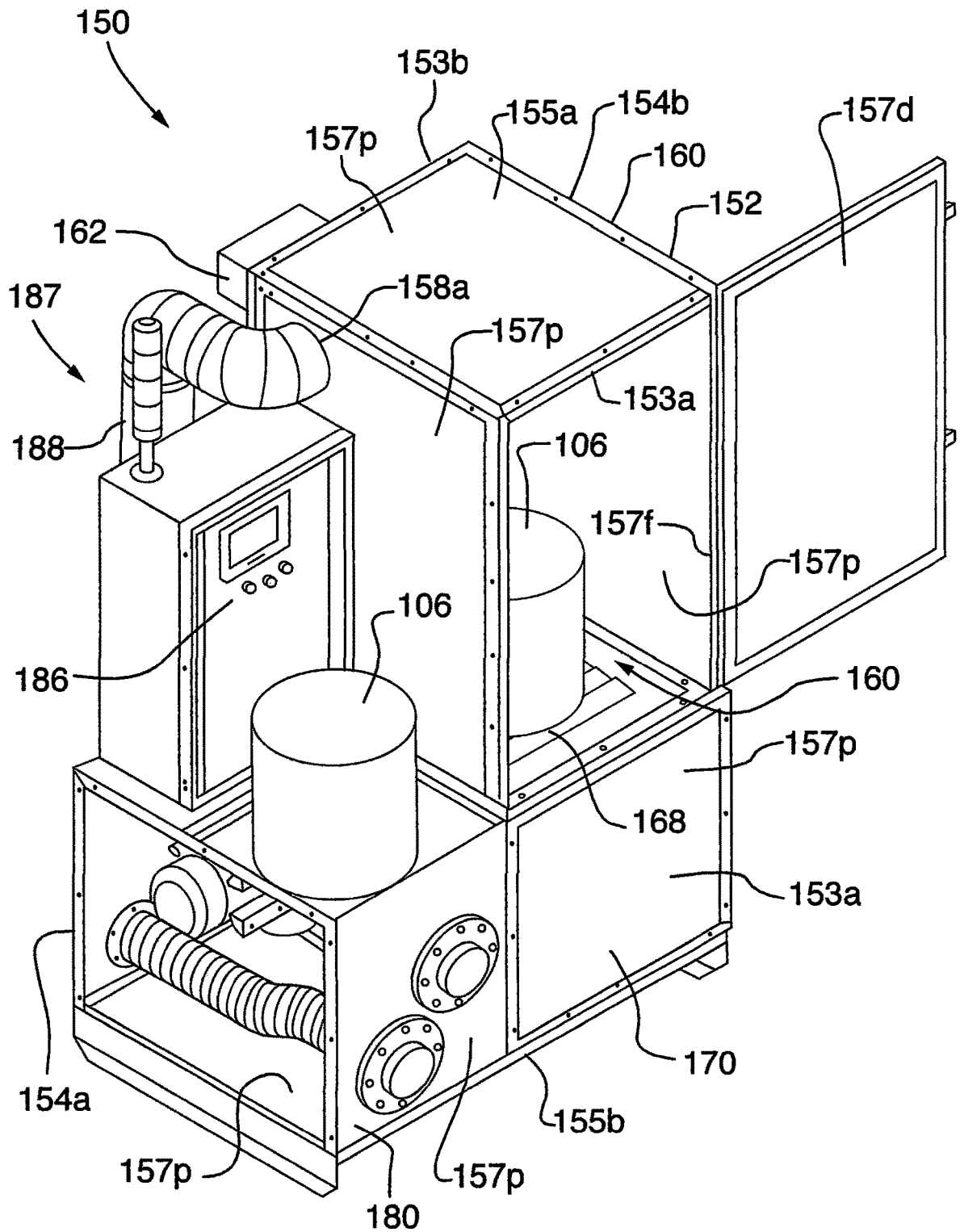

To develop an ideal scaffold for transplantation, it is important that the materials used have suitable mechanical properties for the target tissue as well as biodegradability and biocompatibility. In this study, we chose the PCL polymer for the fabrication of patches because of its established suitability for tissue engineering and application in the biomedical field, including biocompatibility, FDA approval, biodegradability, good flexibility and robust mechanical properties, and relatively easy fabrication process. In addition, we utilized the CFL technology that allows for easily controlling the micro- or nano-topography sizes and structures with scalable and highly reproducible properties. Accordingly, CFL and spin coating were applied to fabricate PCL-based nano-topographically aligned scaffolds with tunable topographic structures and sizes similar to those of the well-organized nano-topographic ECM of the tendon tissue. Using flat-surfaced and nano-patterned PDMS molds, FF and FN patches were fabricated by applying heat and pressure in the CFL lithography process. FIG. 1 shows a schematic of the scaffold fabrication process developed in this study (described in detail in 1.1 in the Materials and Methods section). To improve the hydrophilicity for increasing the cell affinity of the FF and FN patches, the surface of the patches was further treated with $N_2$ gas plasma. The plasma treatment provides a hydrophilic property to polymeric surfaces, which affects cell attachment and cell affinity owing to the production of amine functional groups. FIG. 2 shows a schematic of the plasma treatment process used in this study (described in detail in 1.2 in the Materials and Methods section).

2.2. Characteristics and Properties of $N_2$-FN Patches

Figure 3:
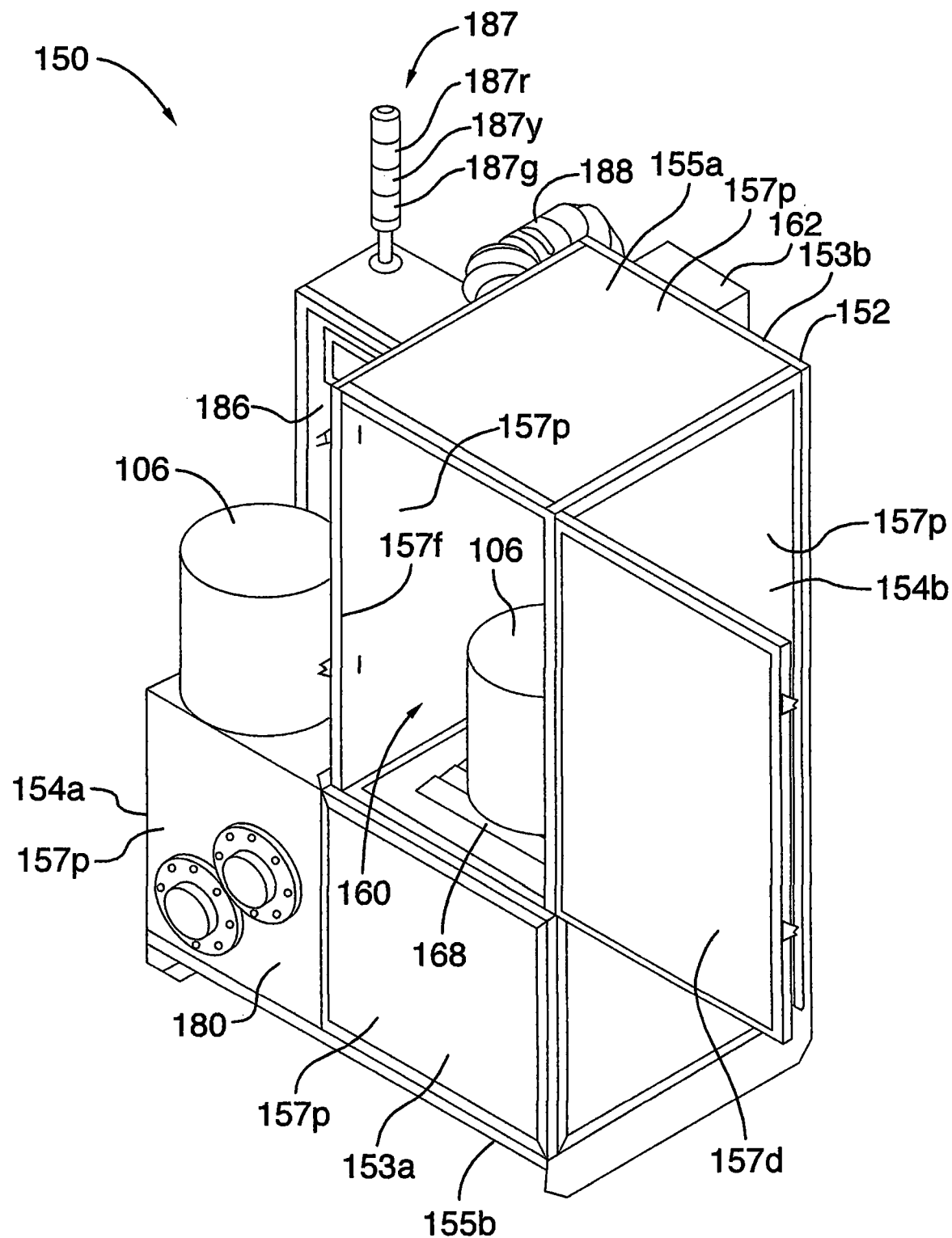
Figure 4:
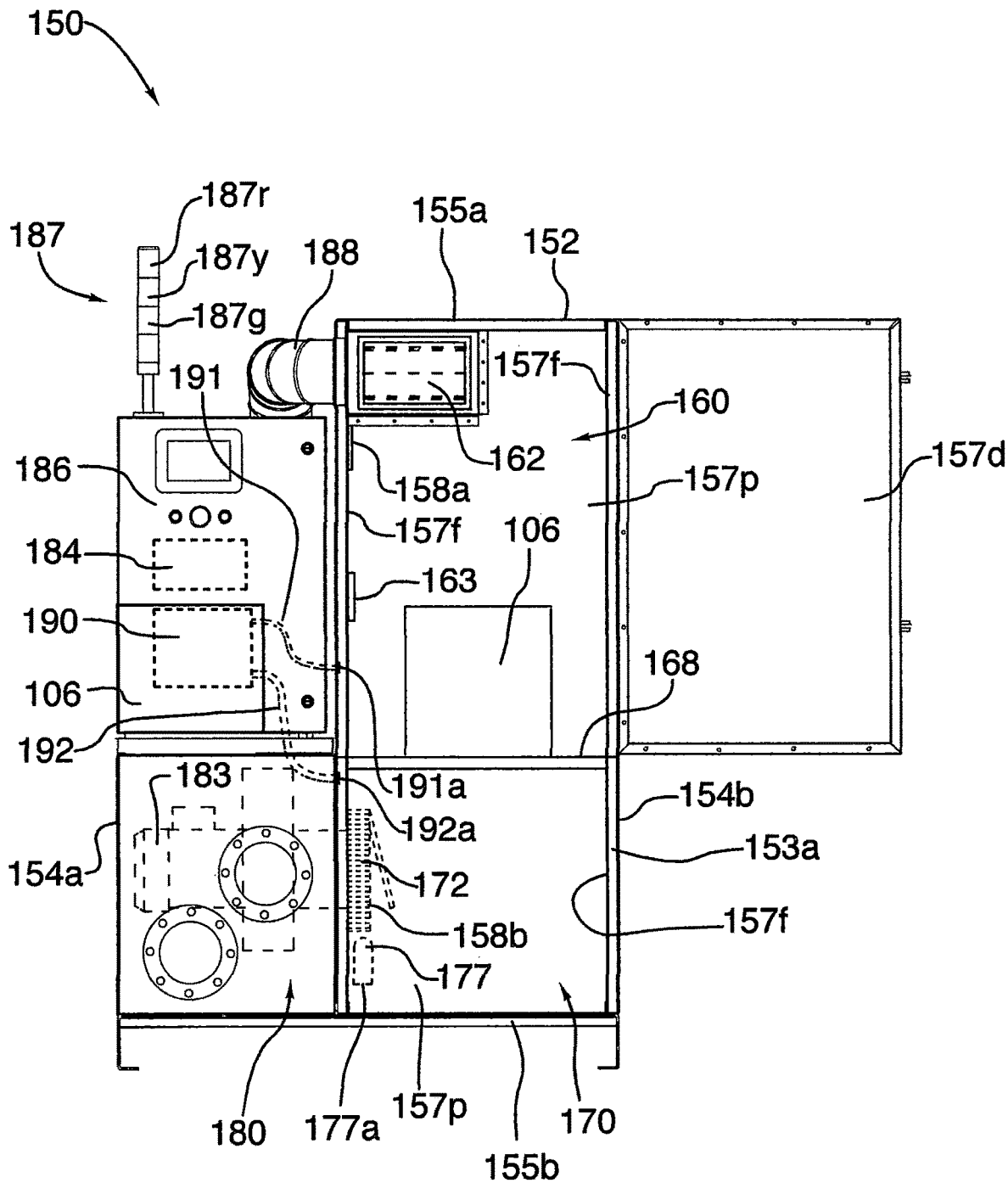
Figure 5:
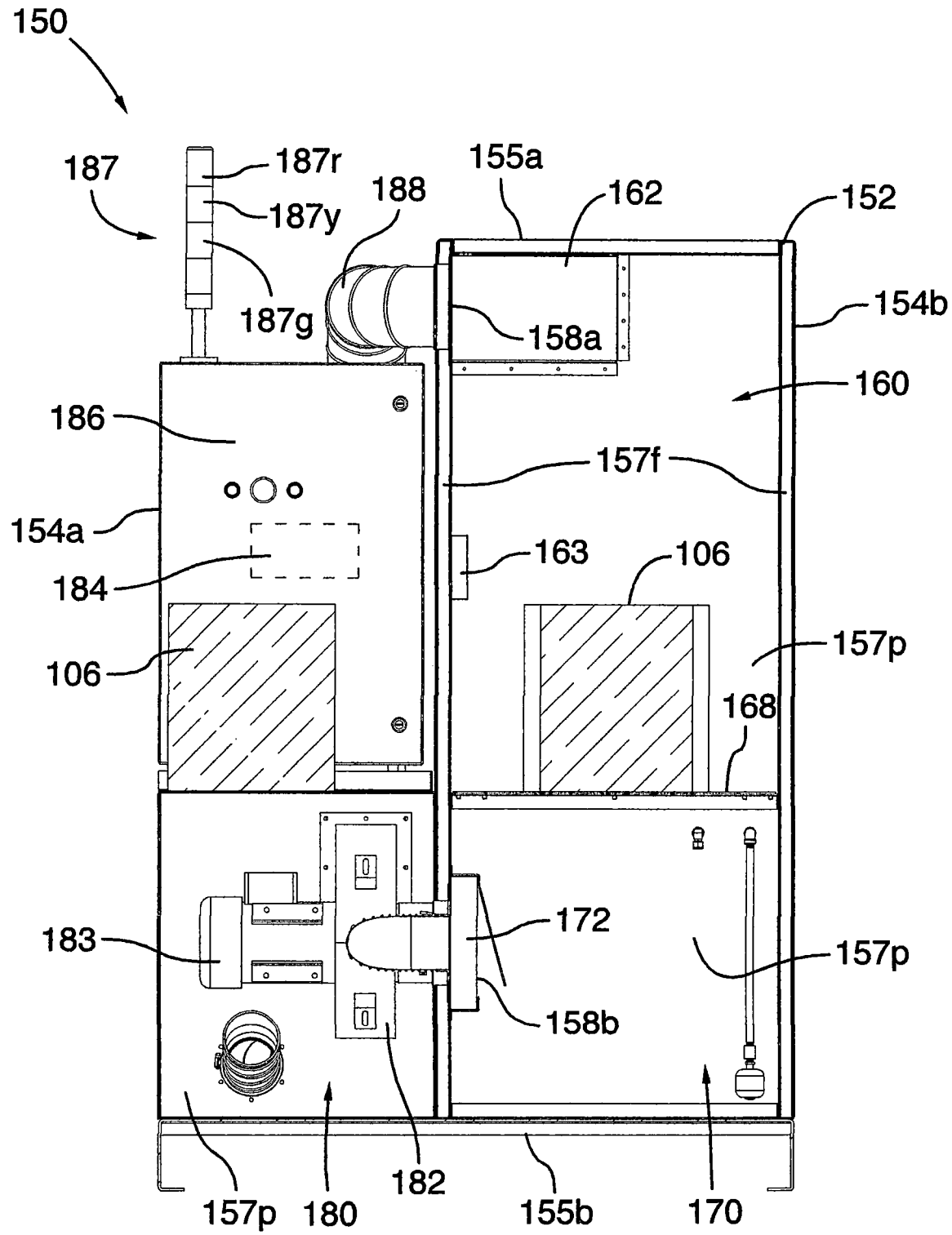
Figure 6:
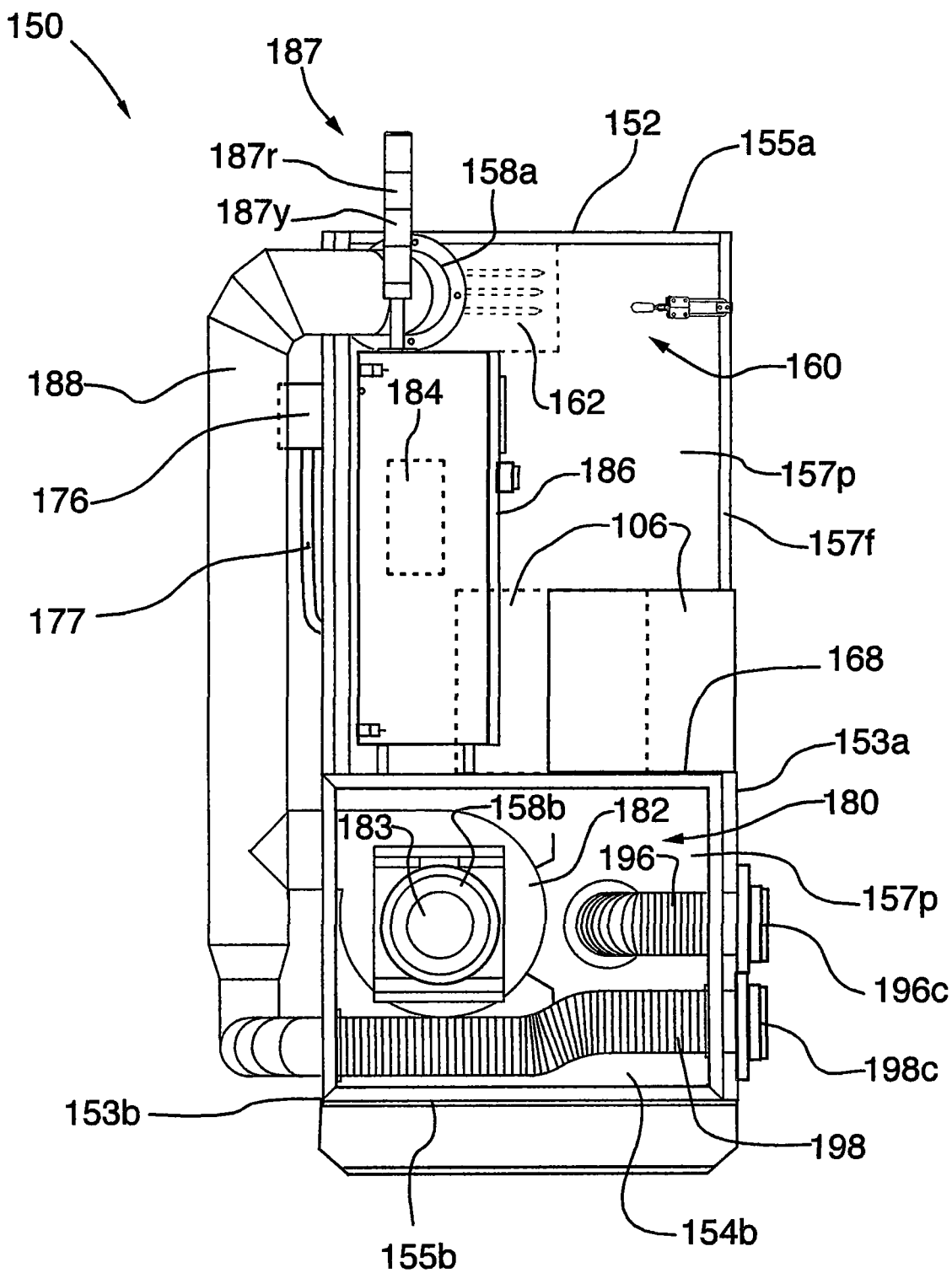
FIGS. 6-8 are effects of N-FN patches on cellular behaviors. (a) Water contact angle measurements of the N-FN treated under various times. (b) Wettability recovery on the surfaces of 30-min N-FN patches. (c) Attachment and proliferation of cells on N-FN patches. Quantitative analysis of cell attachment and proliferation on N-FF patches and N-FN patches showed a gradual increase with plasma treatment time. (d) Effect of N-FN patches on the osteogenic mineralization of tenocytes. Alizarin Red staining and quantification of the degree of osteogenesis showed that the 30-min N-FN patch promoted higher calcium expression levels of tenocytes when compared with other groups. (*$p<0.05$)

SEM images of the surface morphology of N-FN patches revealed a highly aligned topography with grooves and ridges (about 800 nm size), similar to the well-organized topography of the native tendon ECM, without deformation and etching of surfaces with increasing plasma treatment times (FIG. 3). To verify whether the $N_2$ reaction gas and various plasma treatment time conditions used in the plasma treatment process affected PCL properties, the polymer's chemical characteristics were analyzed. The functional groups of plasma-treated patches were investigated by FT-IR spectroscopy (FIG. 4). The characteristic absorption bands related to PCL (i.e., $CH_2$ asymmetric stretching at 2944 $cm^{-1}$, symmetric stretching at 2866 $cm^{-1}$, C=O stretching vibration of carbonyl groups at 1721 $cm^{-1}$, and deformation of C—O at 1161 $cm^{-1}$) were detected in all patches. The chemical changes of the plasma-treated PCL patches compare to the PCL patches were not detected. The surface chemical composition of the N-FN patches was analyzed by XPS. Comparison of the survey scan spectra of FN and N-FN patches showed three separated peaks in all XPS spectra, which correspond to C1s (285 eV), N1s (400 eV), and O1s (532 eV) (FIG. 5). A distinct N1s peak at 400 eV in the N-FN patch spectrum indicated that $N_2$ plasma was successfully applied onto the FN patch. The surface atomic compositions of the FN patch were calculated to be 73.91%, 0.29%, and 25.81% for C1s, N1s, and O1s, respectively. The surface atomic compositions of the N-FN patch were calculated to be 61.83%, 3.34%, and 34.82% for C1s, N1s, and O1s, respectively. The high-resolution XPS N1s spectra of the N-FN patches showed that the N1s peaks of the FN and N-FN patches can be decomposed into a component: one main N—C=O (399.9 eV) (FIG. 5). The atomic configuration of the FN patch was calculated to be 0.51% and those of N-FN was 2.96% for N—C=O. Assessment of wettability of patches through measurement of the water contact angle showed that FN patches has a lower contact angle (82.56±1.8°) when compared with FF patches (88.32±1.7°) (FIG. 6). The water contact angle of both FF and FN patches gradually decreased with increasing $N_2$ plasma treatment time, and the 30-min N-FN patches had a lower contact angle (17±1.4°) than that of 30-min N-FF patches (21±2.1°). To confirm the hydrophobicity variation on the surface after $N_2$ plasma treatment on the FN patch, static contact angle measurements were made at various time points (30 min, 1 h, 2 h, 4 h, 1 day, 2 days, and 6 days) after plasma treatment (FIG. 6). N-FN patches exhibited slight hydrophobic recovery at 30 min to 4 h and showed substantial hydrophobic recovery from 1 day to 6 days after plasma treatment. However, the hydrophilicity of N-FN patches was maintained when compared with the static water contact angle of FN patches.

2.3. In Vitro Analysis of Cell Behavior on N2-FN Patches

Figure 7:
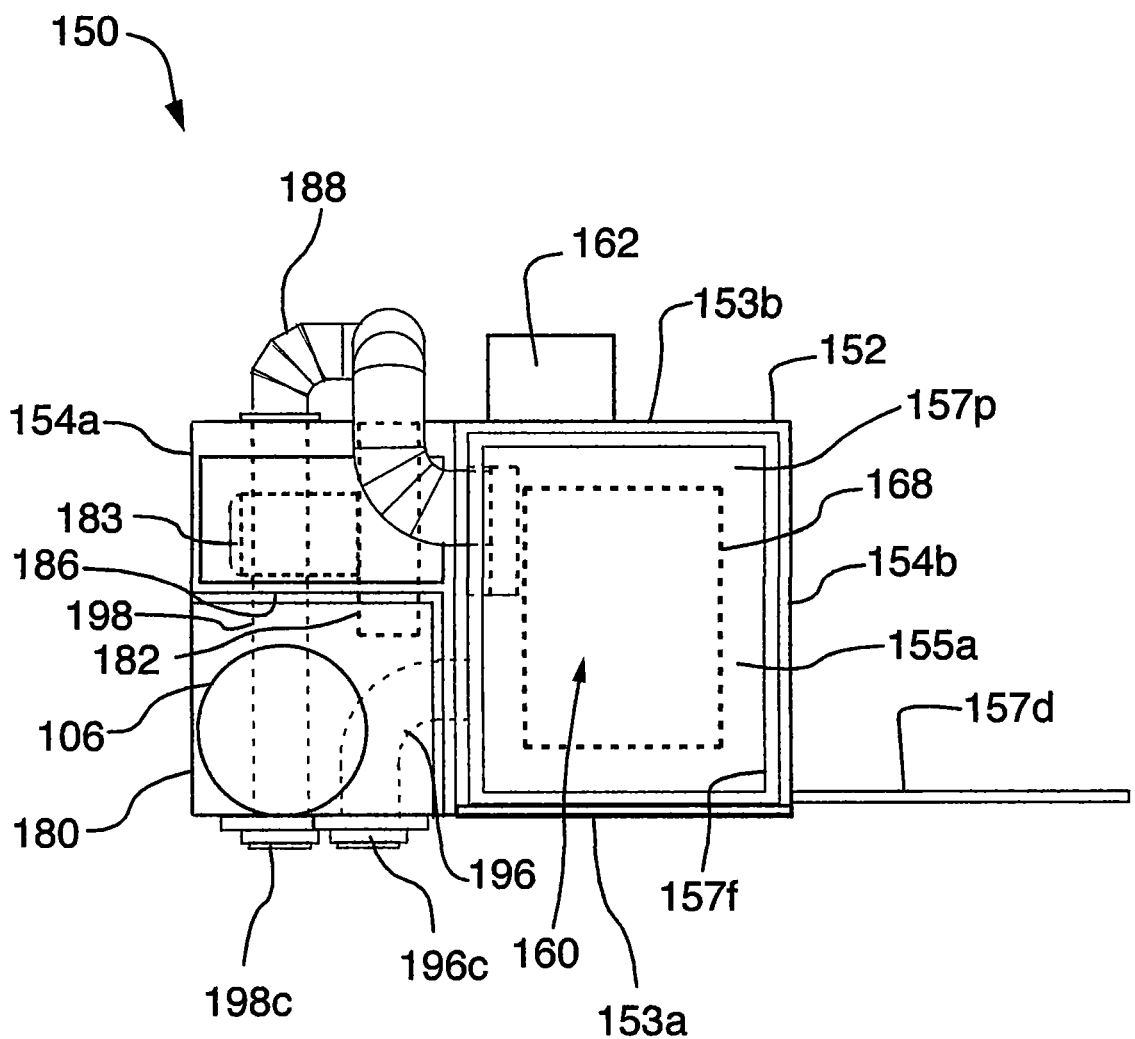
Figure 8:
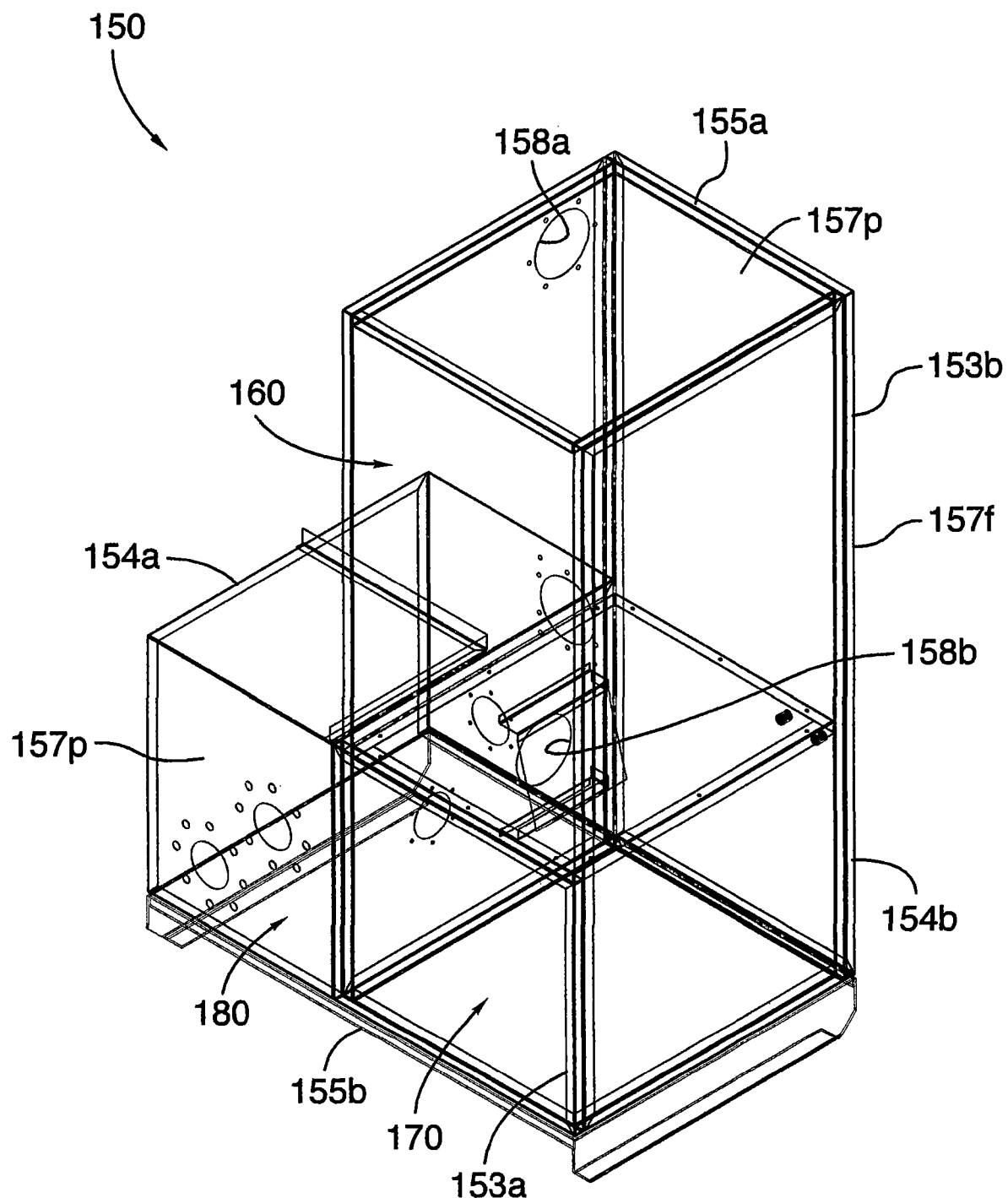

To investigate whether the $N_2$ plasma treatment on the surfaces of FF and FN patches influenced cell proliferation and attachment, we cultured human tenocytes on the patches for 6 h (cell attachment assay), 3 days (cell proliferation assay), and 5 days (cell proliferation assay), respectively (FIG. 7). After 6 h of cell culture, unattached cells were removed by washing with PBS, and cells attached onto the patches were quantified by the WST-1 assay. Tenocytes were well attached on all patches, irrespective of topographic properties, and cells on the 30-min N-FF and N-FN patches showed higher attachment than did those under other plasma treatment times. After 3 days and 5 days of cell culture, cell proliferation was higher on the 30-min plasma treatment patches when compared with those of the other groups (FIG. 7). The osteogenic mineralization of tenocytes on the N-FN patches was examined by culturing cells on the two scaffolds in osteogenic induction medium for 14 days. Alizarin Red staining (FIG. 8) revealed slightly higher calcium expression levels on the 30-min N-FN patches than on other samples and the tissue culture polystyrene substrate (TCPS). Although the N-FN patches treated for 30 min showed the highest degree of quantification on the osteogenic mineralization, there was no significant difference from the other control groups.

2.4. Design and Fabrication of $O_2$-FMN Patches

Figure 9:
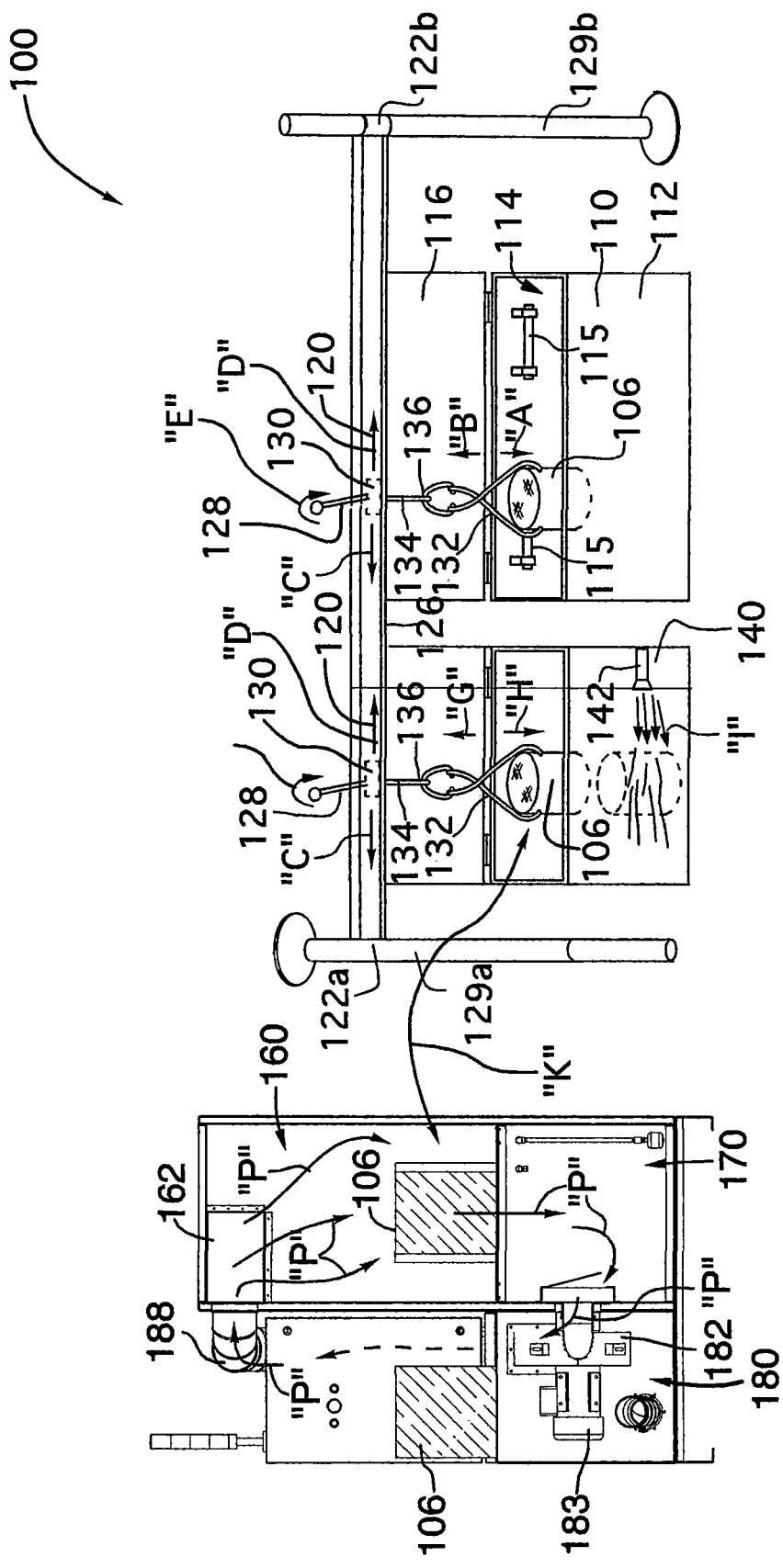
FIGS. 9-15 are characterizations of the O-FN patch and effect of the O-FN patch on cellular behaviors. (9) Schematic of plasma surface modification using $O_2$ plasma reaction gas on the surface of the FN patch. (10) SEM images of the O-FMN patch under various treatment times. The surface topography of the O-FMN patch showed generation of nanopore structures without damage to the aligned nano-topography. (11) FT-IR analysis of the 30-min O-FMN. (12) XPS survey scans and high-resolution O1s XPS spectra of FN patches and 30-min O-FMN patches. (13) Water contact angle measurements and wettability recovery on surfaces of the O-FMN patch. (14) Attachment and proliferation of cells on O-FMN patches. After 5 days of cell culture, cell proliferation was higher on the 30-min O-FMN than on the 30-min N-FN. (15) Effect of O-FMN patches on the osteogenic mineralization of tenocytes. Alizarin Red staining revealed higher calcium expression levels on the 30-min O-FMN patches than on other samples and the tissue culture polystyrene substrate (TCPS). Quantification of osteogenic mineralization demonstrated the highest degree of osteogenesis by the cells on the 30-min O-FMN patches. (*$p<0.05$)

Various reaction gases such as $N_2$, $O_2$, air, and $NH_3$ have been used in plasma treatment for polymeric surface modification. Among the various methods for the surface modifications of biomaterials, $O_2$ plasma surface modification has been proven as an effective and inexpensive strategy to alter physicochemical, mechanical, and biological properties such as roughness, wettability, hardness, and biocompatibility by the volatilization and formation of functional groups due to chemical bonding. In addition, $O_2$ plasma has been used to produce carboxyl, carbonyl, and hydroxyl functional groups onto the surface of various polymers and to improve cell attachment, proliferation, and differentiation. As described above, $N_2$-FN patches enhanced cell proliferation and differentiation owing to increased affinity to the patch because of the improved hydrophilicity of the surface. Therefore, we also designed $O_2$-FMN patches to generate a nanoporous structure to further improve the hydrophilicity and cell affinity of the FN patch. FIG. 9 shows a schematic of the plasma treatment process used in this study (described in detail in the Materials and Methods section).

2.5. Characteristics and Properties of $O_2$-FMN Patches

Figure 10:
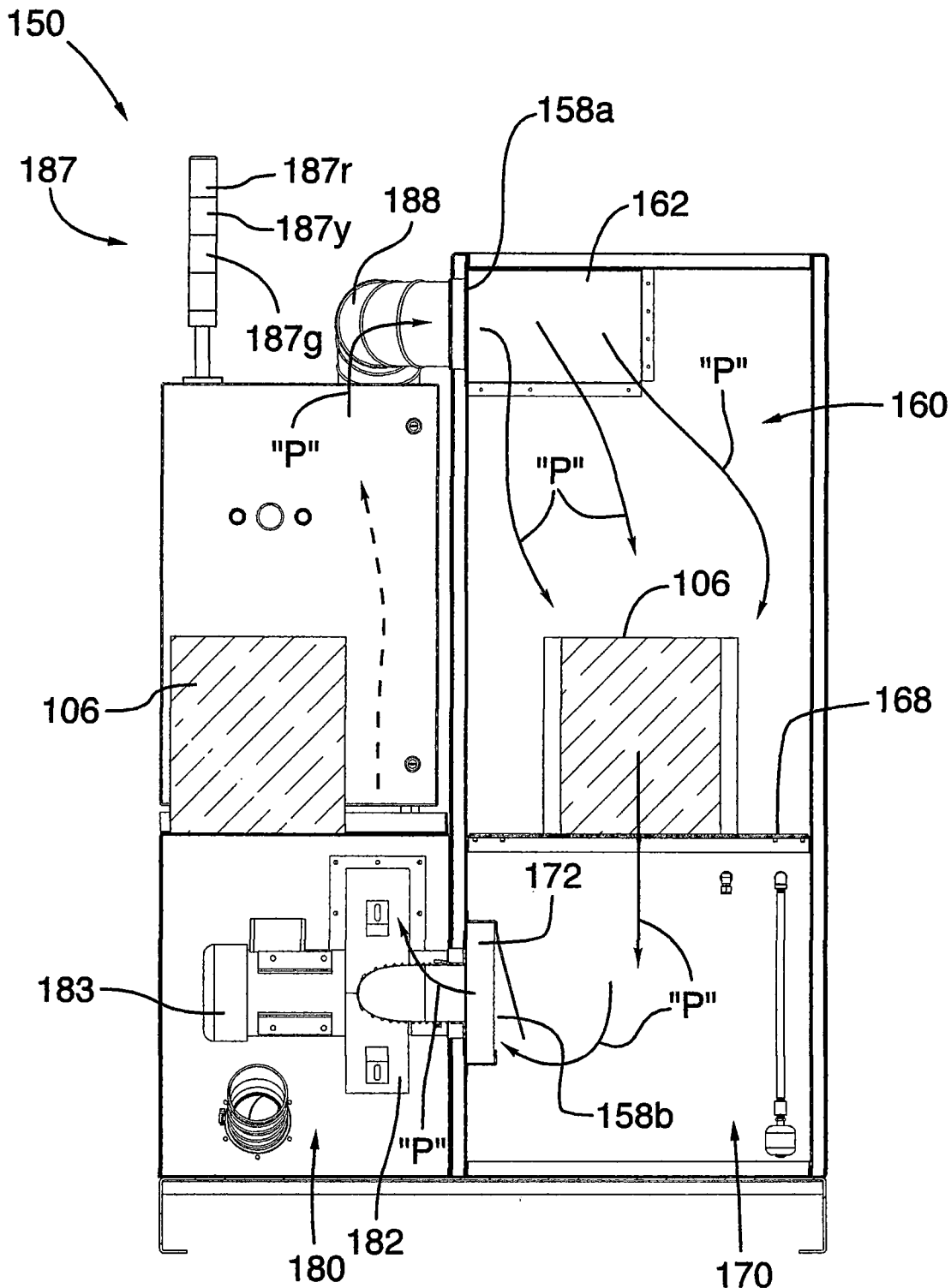

SEM images of the surface morphology of the O-FMN patches revealed a highly aligned topography with grooves and ridges, similar to the well-organized topography of the tendon ECM (FIG. 10). Nano-sized pores generated by $O_2$ plasma treatment for 30 min were observed due to etching and volatilization, which were not generated in the N-FN patches. Also, O-FMN patches showed the various pore sizes and numbers depending on the $O_2$ plasma treatment time; however, these pores did not result in notable deformation to the highly aligned nano-topography. This result indicated that generation of nano-sized pores onto the aligned nano-topography could form multi-scale nanostructures similar to the complex microenvironment of the ECM. Thus, we hypothesized that the combination of multi-scale nanostructures comprising nanopores and a well-defined nano-topography and functional groups applied by $O_2$ plasma treatment would provide a physiochemically synergetic effect to improve cell affinity along with cell function and tissue regeneration.

Figure 11:
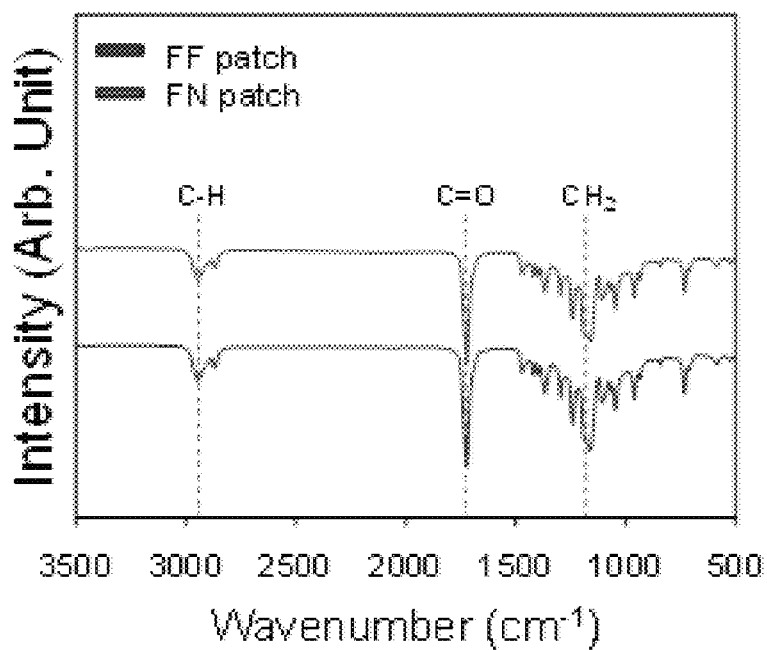
Figure 12:
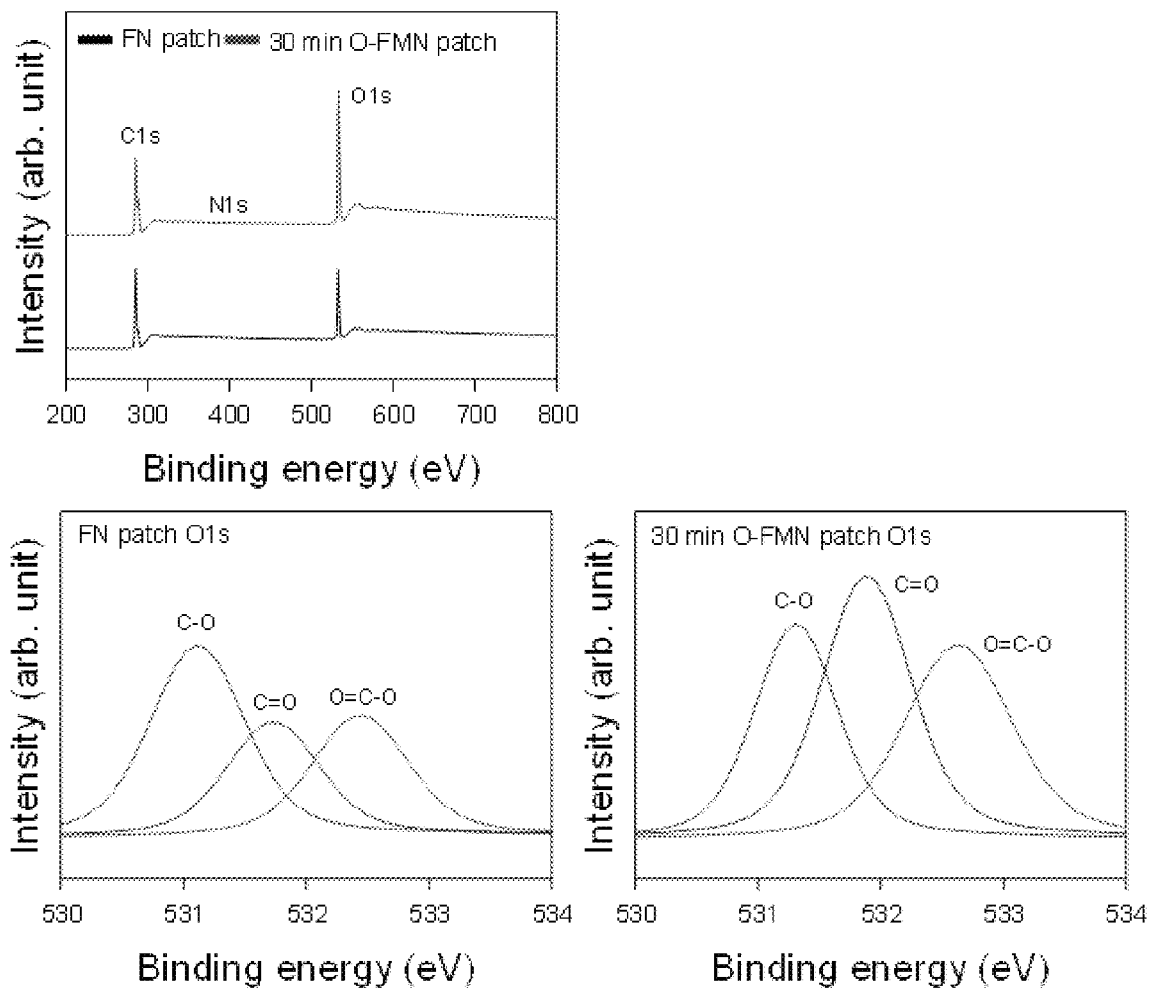
Figure 13:
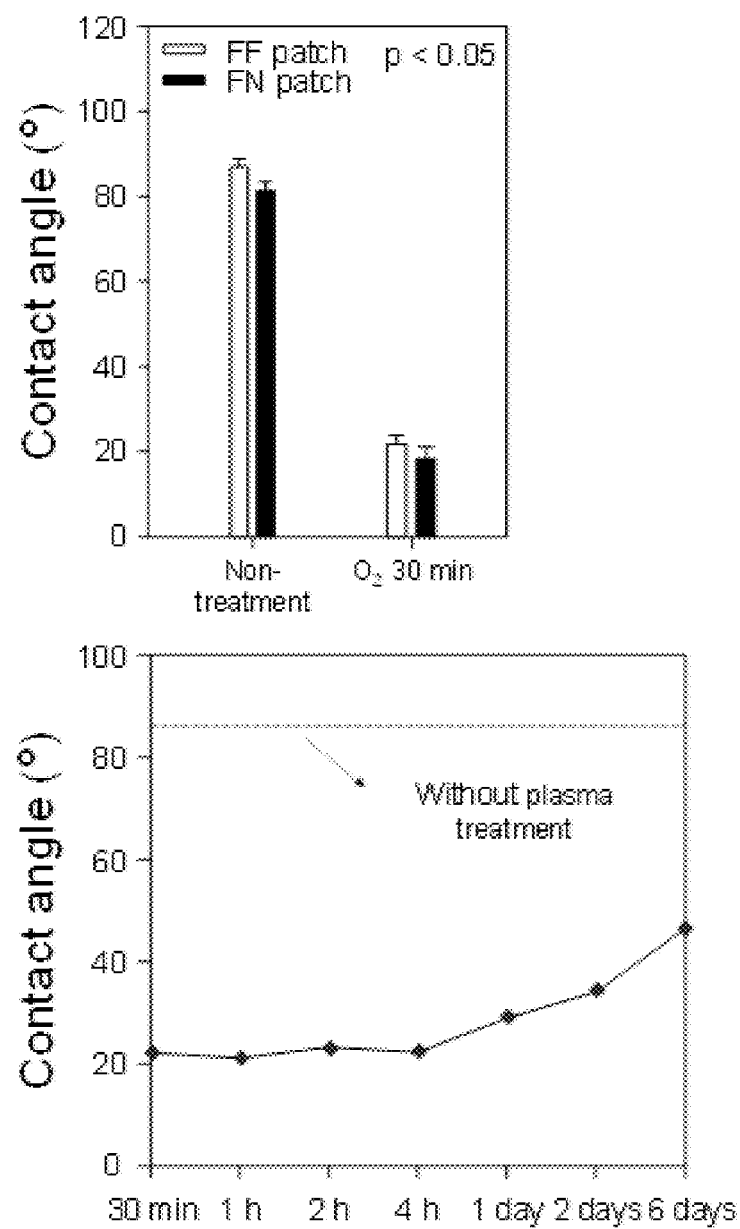

To verify whether the $O_2$ reaction gas used in the plasma treatment process changed PCL properties, the polymer's chemical characteristics were analyzed. The functional groups of the O-FMN patch were investigated by FT-IR spectroscopy (FIG. 11). The characteristic absorption bands related to PCL (i.e., $CH_2$ asymmetric stretching at 2944 $cm^{-1}$, symmetric stretching at 2866 $cm^{-1}$, C=O stretching vibration of carbonyl groups at 1721 $cm^{-1}$, and deformation of C—O at 1161 $cm^{-1}$) were detected in all patches, indicating that functional groups were well maintained and were not affected by plasma treatments. The surface chemical composition of the O-FMN and FN patches was analyzed by XPS. As shown in FIG. 12, all XPS spectra had three separated peaks corresponding to C1s (285 eV), N1s (400 eV), and O1s (532 eV). A distinct O1s peak at 532 eV in the O-FMN patch spectrum indicated that the $O_2$ plasma had been successfully applied onto the FN patch. The surface atomic compositions of the FN patch were calculated to be 73.91%, 0.29%, and 25.81%, and those of the O-FMN patch were calculated to be 63.7%, 0.23%, and 36.07% for C1s, N1s, and O1s, respectively. The high-resolution XPS O1s spectra showed that the O1s peak of the FN and O-FMN patches can be decomposed into three components: C—O component (531.69 eV) and C=O (532.39 eV), and O=C—O (533.3 eV) components (FIG. 12). The atomic configurations of the FN patch were calculated to be 11.7%, 6.83%, and 7.49% for C—O, C=O, and O=C—O, respectively. The atomic configurations of the O-FMN patch were calculated to be 10.29%, 13.48%, and 11.97% for C—O, C=O, and O=C—O, respectively. The wettability of the O-FF and O-FMN patches were evaluated by water contact angle measurement, showing that FN patches had a lower contact angle (82.56±1.8°) than FF patches (88.32±1.7°) (FIG. 13). Similar to the N-FF and N-FN patch, the water contact angle of O-FF and O-FMN patches after plasma treatment were decreased, and 30-min O-FMN patches had a lower contact angle (18.4±1.1°) than did 30-min O-FF patches (22.01±2.2°). To confirm the hydrophobicity variation on the surface of O-FMN patches, the static contact angle measurements were conducted over $O_2$ plasma treatment time (30 min, 1 h, 2 h, 4 h, 1 day, 2 days, and 6 days). As shown in FIG. 13, O-FMN patches exhibited small hydrophobic recovery at 30 min to 4 h and substantial hydrophobic recovery at 1 day to 6 days after plasma treatment. However, the hydrophilicity of the O-FMN patch was well maintained compared with the high static water contact angle of FN patches.

2.6. In Vitro Cell Behaviors on $O_2$-FMN Patches

Figure 14:
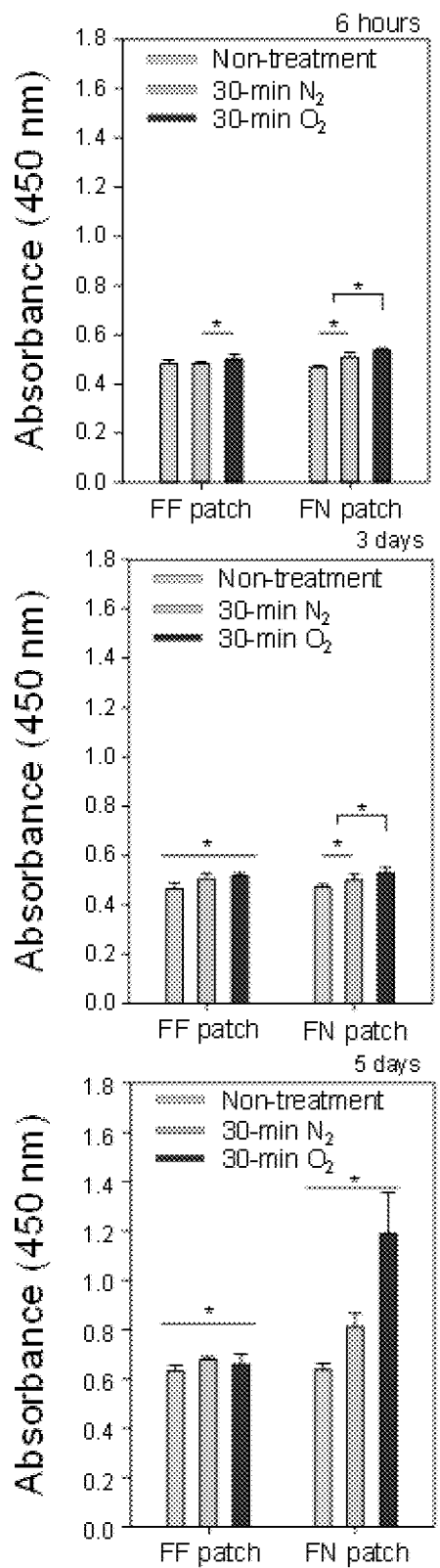
Figure 15:
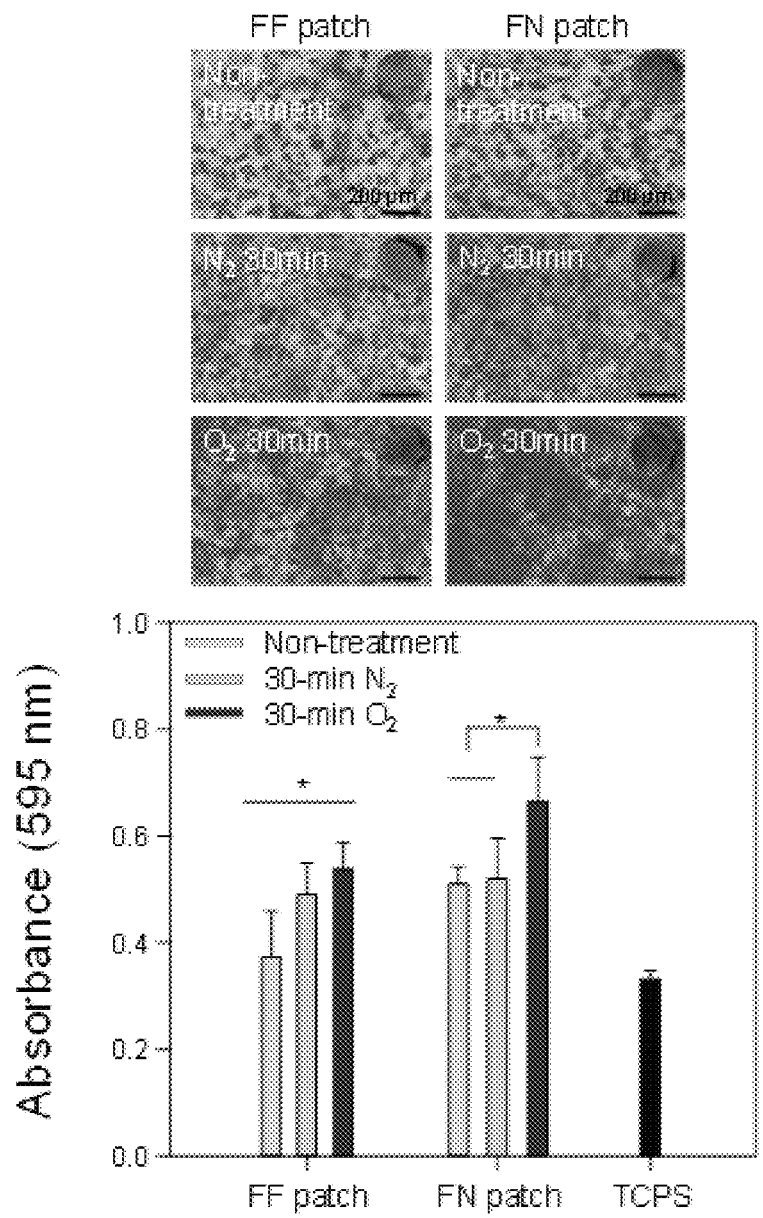

Cell attachment and proliferation on N-FN and O-FMN patches were both higher than those on FF patches. In addition, after 5 days of cell culture, cell proliferation was considerably higher on O-FMN patches treated with $O_2$ plasma for 30 min than that observed on 30-min N-FN patches (FIG. 14). This suggests that the surface modified by $O_2$ plasma may provide various cell-friendly chemicals and hierarchically topographical environments that are similar to the complex microenvironment of the ECM, thus promoting the proliferation and attachment of tenocytes when compared with the surface modified by $N_2$ plasma. In addition, we examined the osteogenic mineralization of tenocytes on the N-FN and O-FMN patches by culturing cells in osteogenic induction medium for 14 days. Alizarin Red staining (FIG. 15) revealed higher calcium expression levels on the O-FMN patches for 30 min than on N-FF and N-FN patches for 30 min and the TCPS. Quantification of osteogenic mineralization further demonstrated the highest degree of osteogenesis by cells cultured on the 30-min O-FMN patches. These results suggest that plasma treatment of FN patches may provide cell-friendly chemicals and topographical environments to enhance the attachment, proliferation, and differentiation of tenocytes. Therefore, the highly aligned nano-topography, generation of nano-sized pores, and various functional groups induced by plasma treatment using $O_2$ gas synergistically contributed to the proliferation and differentiation of tenocytes.

2.7. In Vivo Animal Study

Figure 16:
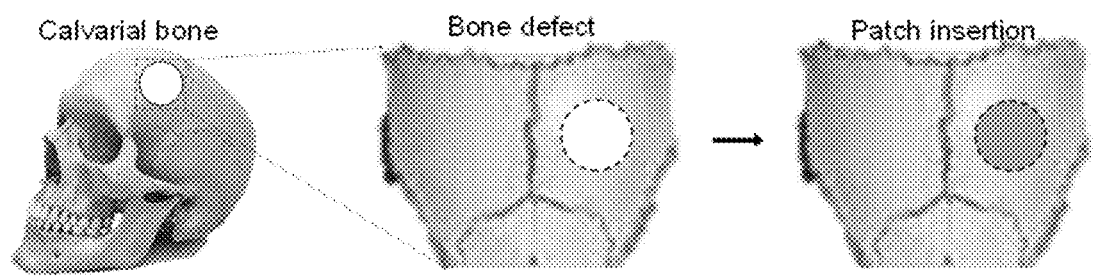
FIGS. 16-19 are effects of the O-FMN patches on bone tissue regeneration. (16) Surgical procedure for rat calvarial bone repair. (17) Representative histologic images of H&E staining of the insertion site of FN, N-FN, and O-FMN patches onto rat calvarial bone 6 weeks after repair. (18) Representative micro-CT image after 3 and 6 weeks of repair. (19) Quantitative analysis of bone volume and area of the bone regeneration site after 3 and 6 weeks of repair. (*$p<0.05$)
Figure 17:
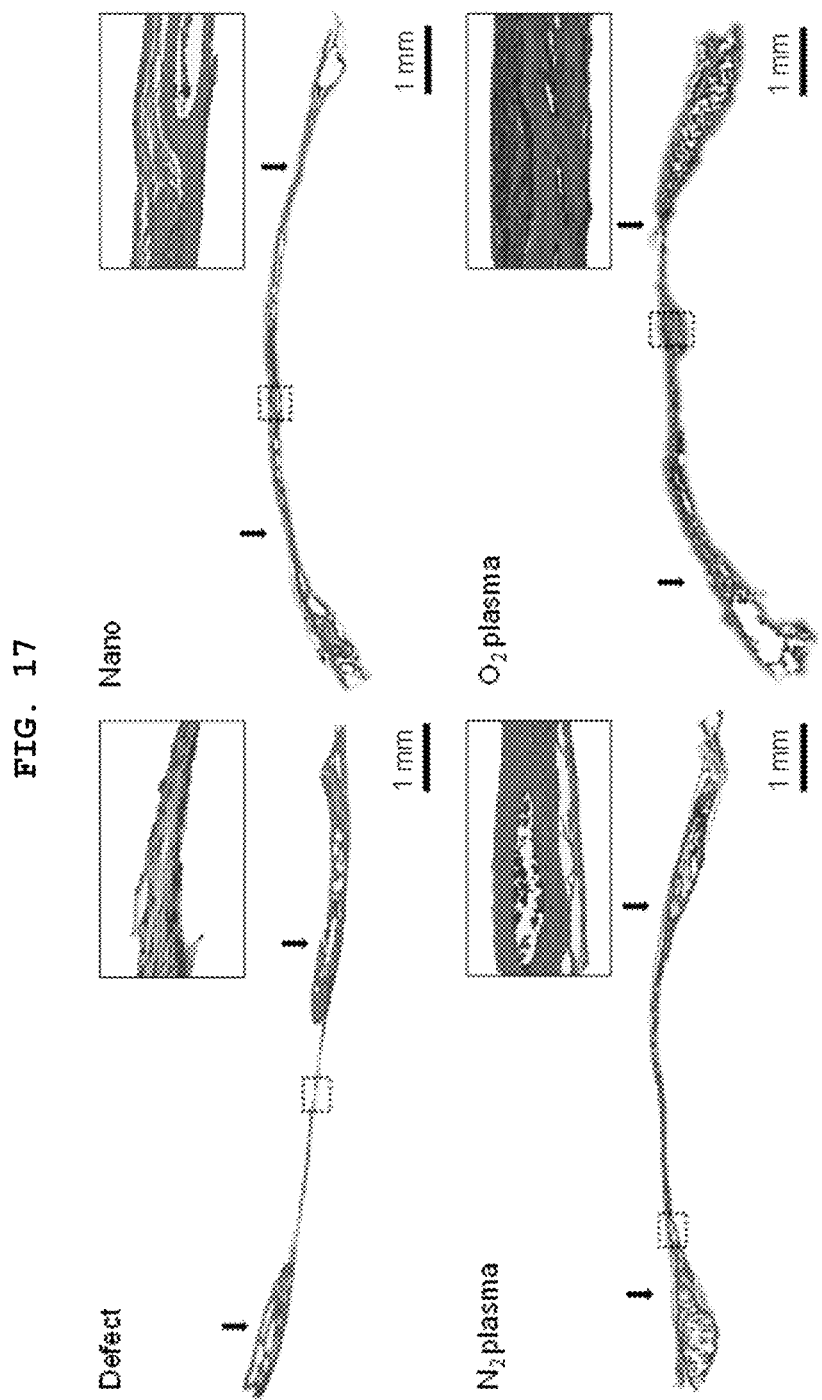

In addition, we confirmed effects of $N_2$ and $O_2$ plasma treatment and nanotopograhpy throughout the bone regeneration in vivo (FIG. 16). All mice used in the in vivo studies survived to the sacrifice date, and no adverse reaction was observed. FN patch, N-FN and O-FMN patch with were engrafted onto the calvarial bone defect with 5 mm diameter (FIG. 16). No infection or inflammatory reaction were observed in any of the mouse throughout the postoperative period. The patches remained for 6 weeks without deformation. To confirm the bone regeneration efficacy from $N_2$ and $O_2$ plasma treatment and nanotopograhpy, we conducted the hematoxylin and eosin (H&E) staining at 6 weeks after implantation (FIG. 17). As the results, the bone of defect groups was empty in the defect area. This confirmed that more bone formation and a dense cytoplasm occurred in the O-FMN patch compared to other groups.

Figure 20:
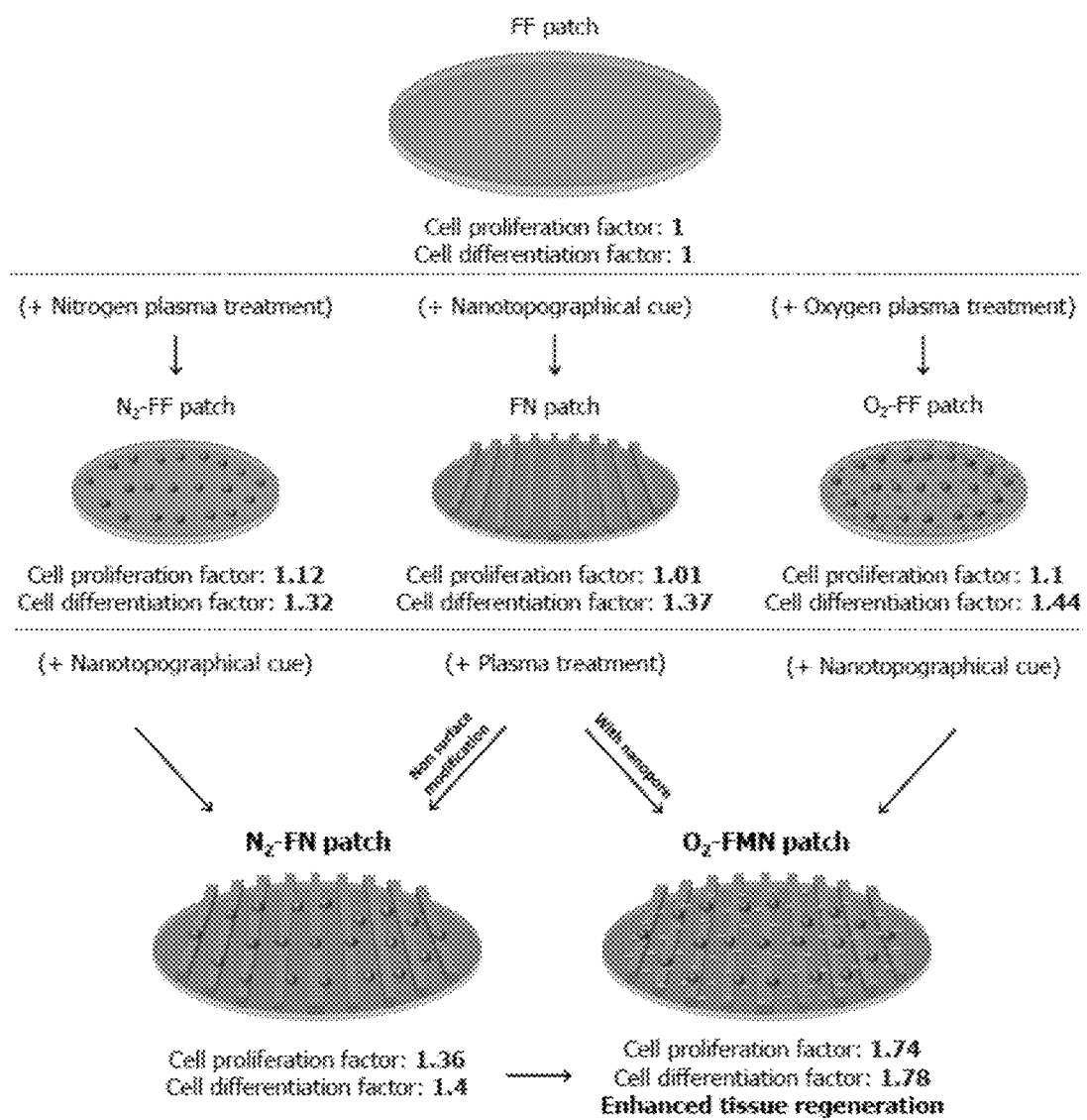
FIG. 20 is a schematic view illustrating synergistic effects of the nanotopographic structure and $O_2$ plasma treatment on proliferation and osteogenic mineralization of fibroblasts.

Based on the qualitative histologic analysis on effect of O-FMN patch presented as strategy for repair of RC tendon tissue tear, semi quantitative histology analysis was performed using Bonar scoring system (FIG. 20). Cell morphology, ground substance, collagen arrangement, and vascularity changes were observed in all groups and were graded depending on Bonar score. The cell morphology and collagen arrangement scores of O-FMN patch group were significantly lower than those of other groups (FIG. 20). The ground substance and vascularity scores of O-FMN patch group were similar to the score of the O-FF patch group but were significantly lower than those of other patch groups. Overall, the total histological score of O-FMN patch group was significantly lower than those of other patch groups (FIG. 20). These results indicate the importance of the oxygen plasma treatment, a precisely aligned nanotopography, and the nanoporous structures in synthetic ECMs for guiding tendon tissue and fibrocartilage regeneration.

Figure 18:
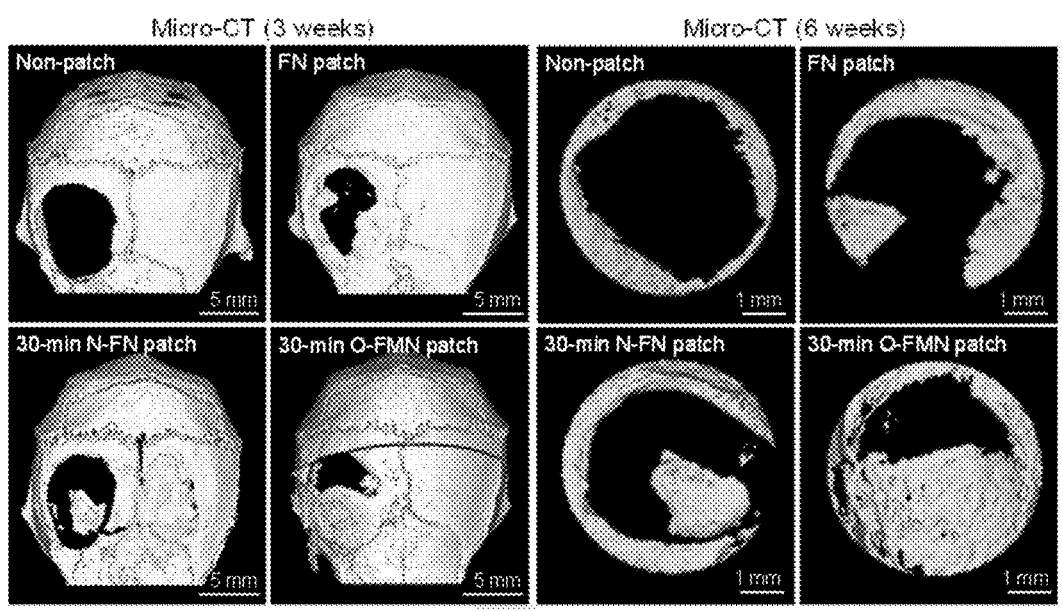
Figure 19:
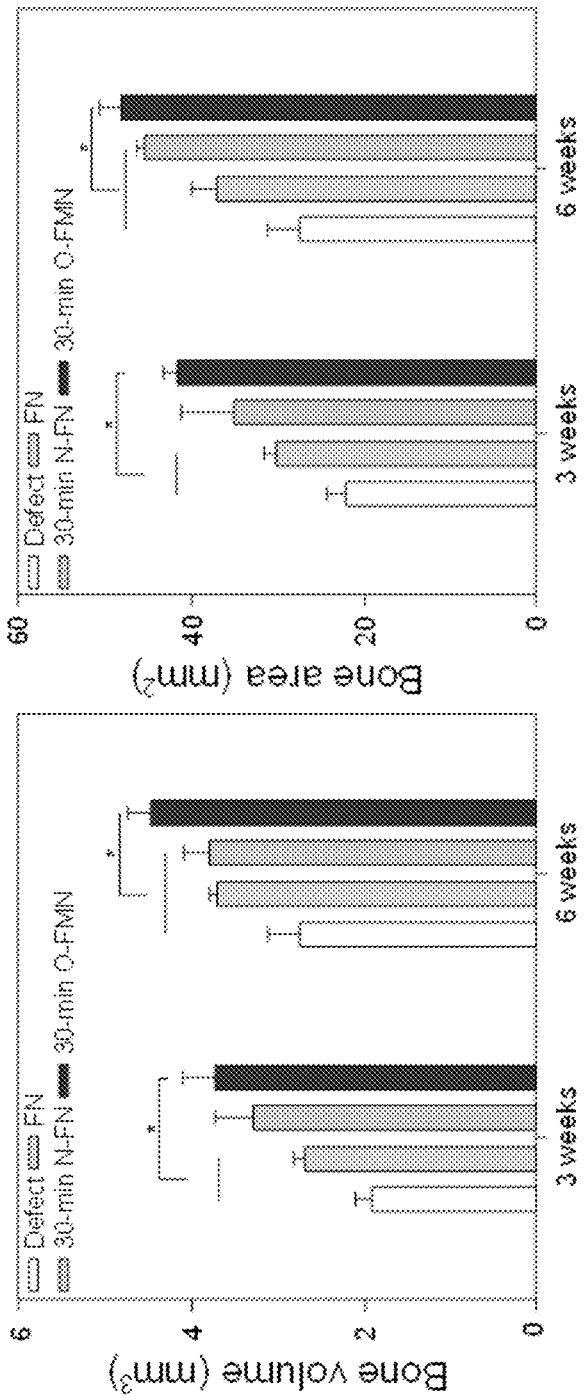

For quantitative assessment of effect of the nanotopography and plasma treatment on the bone formation we performed micro-CT and 3D-image conversion using the MIMICS 14.0 software on new bone defects in vivo. As shown in the 3D images (FIG. 18), bone formation in the nanotopography and plasma-treated patches occurred along the periphery of the bone defect and grew along the patches. After 3, 6 weeks, the compact bone formation was not observed in the defect group, FN patch groups, and N-FN groups whereas bone regeneration was significantly enhanced in the O-FMN patch groups after 3, 6 weeks of implantation. The new bone formation was observed from edge to center depending on nanotopograhpy direction. At the 6 weeks, the bone volume was 1.91 $mm^3$ in the defect group, 2.43 $mm^3$ in the FN patch groups, and 3.38 $mm^3$ in the N-FN patch groups and 4.25 $mm^3$ in the O-FMN patch groups (FIG. 19). The bone area was 19.81 $mm^2$ in the defect groups, 26.09 $mm^2$ FN patch groups, 37.92 in the N-FN patch groups and 47.92 $mm^2$ in the O-FMN patch groups (FIG. 19). The results of bone regeneration and formation provide insight into the importance of nanotopography and $O_2$ plasma treatment cues for inducing bone tissue regeneration.

2.8. Quantitative Investigation of Relative Contributions

Based on these in vitro and in vivo results, we quantified the capability of tissue regeneration and cell function enhanced by the beneficial effects of the O-FMN patch on proliferation and differentiation (FIG. 20). Quantitative investigation of relative contributions was derived from by setting the raw average values of the proliferation and osteogenic mineralization absorbance of the FF patch as 1, and calculating relatively the absorbance of the FN, N-FF, N-FN, O-FF, O-FMN. The aligned nanostructure of the FN patch, functional groups applied by $N_2$ plasma treatment, and nano-sized pores and functional groups generated by the $O_2$ plasma treatment could only promote proliferation by a factor of 1.01, 1.12, and 1.1, respectively, and osteogenic differentiation was promoted by a factor of 1.37, 1.32, and 1.44, respectively. The combination of a nano-topography and $N_2$ plasma treatment increased proliferation and osteogenic differentiation by a factor of 1.36 and 1.4, respectively. In addition, the combination of nano-topography and $O_2$ plasma treatment significantly increased the proliferation and osteogenic differentiation by a factor of 1.74 and 1.78, respectively, further confirming the enhanced effects of highly aligned nano-topography, nano-sized pores, and functional groups. This synergetic effect may be due to improvement in cell topography or cell-cell interactions from the highly aligned nano-topography and nano-sized pores generated by $O_2$ plasma treatment.

What is claimed is:

1. A scaffold for tissue regeneration, the scaffold comprising:
    a plurality of nitrogen or oxygen plasma-treated grooves and ridges on one surface thereof,
    wherein the grooves or ridges have a plurality of nanopores formed thereon,
    wherein the nanopore has a diameter of 50 to 200 nm.

2. The scaffold according to claim 1, wherein the grooves and the ridges extend in one direction.

3. The scaffold according to claim 1, wherein the grooves and the ridges have a width of 100 to 900 nm, respectively.

4. The scaffold according to claim 1, wherein a ratio of widths of the grooves and the ridges is 1:0.5 to 1.5.

5. The scaffold according to claim 1, wherein the ridge has a height of 100 to 900 nm from the groove.

6. The scaffold according to claim 1, wherein the one surface has a carboxyl group (O=C—O), a carbonyl group (C=O), or a hydroxyl group (—OH).

7. The scaffold according to claim 1, wherein the scaffold is made of one or more materials selected from the group consisting of polyurethane acrylate (PUA) resin, polyvinyl alcohol resin, polyethylene resin, polypropylene resin, polyethylene glycol resin, poly (L-lactide-co-glycolide) resin, polycaprolactone (PCL) resin, polylactic acid (PLA) resin, polyglycolic acid (PGA) resin, chitosan, gelatin, collagen, and a combination thereof.

8. The scaffold according to claim 1, wherein the tissue is epithelial tissue, muscle tissue, tendon tissue, bone tissue or cartilage tissue.

9. The scaffold according to claim 1, wherein the nitrogen or oxygen plasma-treated grooves and ridges are the nitrogen plasma-treated grooves and ridges.

10. The scaffold according to claim 1, wherein the nitrogen or oxygen plasma-treated grooves and ridges are the oxygen plasma-treated grooves and ridges.

11. The scaffold according to claim 1, wherein the scaffold is made of polycaprolactone (PCL) resin.

12. A method of manufacturing a scaffold for tissue regeneration comprising:

forming a plurality of nitrogen or oxygen plasma-treated grooves and ridges on one surface of a base film; and performing oxygen plasma treatment on the one surface of the base film to form a plurality of nanopores on the one surface, wherein the nanopore has a diameter of 50 to 200 nm.

13. The method according to claim 12, wherein the base film is one or more materials selected from the group consisting of polyurethane acrylate (PUA) resin, polyvinyl alcohol resin, polyethylene resin, polypropylene resin, polyethylene glycol resin, poly (L-lactide-co-glycolide) resin, polycaprolactone (PCL) resin, polylactic acid (PLA) resin, polyglycolic acid (PGA) resin, chitosan, gelatin, collagen, and a combination thereof.

* * * * *